United States Patent
Cluff et al.

(10) Patent No.: US 10,765,690 B2
(45) Date of Patent: Sep. 8, 2020

(54) TLR4 AGONISTS AND COMPOSITIONS THEREOF AND THEIR USE IN THE TREATMENT OF CANCER

(71) Applicant: GlaxoSmithKline Intellectual Property Development Limited, Brentford, Middlesex (GB)

(72) Inventors: Christopher W. Cluff, Hamilton, MT (US); Hua-Xin Gao, Collegeville, PA (US)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 19 days.

(21) Appl. No.: 15/749,854

(22) PCT Filed: Jun. 3, 2016

(86) PCT No.: PCT/IB2016/053290
§ 371 (c)(1),
(2) Date: Feb. 2, 2018

(87) PCT Pub. No.: WO2017/021792
PCT Pub. Date: Feb. 9, 2017

(65) Prior Publication Data
US 2018/0221399 A1    Aug. 9, 2018

Related U.S. Application Data

(60) Provisional application No. 62/201,912, filed on Aug. 6, 2015.

(51) Int. Cl.
| | |
|---|---|
| *A61K 31/7032* | (2006.01) |
| *A61P 35/00* | (2006.01) |
| *A61K 31/407* | (2006.01) |
| *A61K 45/06* | (2006.01) |
| *A61K 31/675* | (2006.01) |
| *A61K 9/00* | (2006.01) |
| *A61K 39/395* | (2006.01) |
| *C07K 16/28* | (2006.01) |
| *A61K 39/00* | (2006.01) |

(52) U.S. Cl.
CPC ........ *A61K 31/7032* (2013.01); *A61K 9/0019* (2013.01); *A61K 31/407* (2013.01); *A61K 31/675* (2013.01); *A61K 39/3955* (2013.01); *A61K 45/06* (2013.01); *A61P 35/00* (2018.01); *C07K 16/2818* (2013.01); *A61K 2039/505* (2013.01)

(58) Field of Classification Search
None
See application file for complete search history.

(56) References Cited

U.S. PATENT DOCUMENTS

| 8,741,295 B2 * | 6/2014 | Olive | C07K 16/2827 424/141.1 |
|---|---|---|---|
| 2003/0147920 A1 | 8/2003 | Mossman et al. | |
| 2005/0227943 A1 | 10/2005 | Johnson et al. | |
| 2012/0321694 A1 | 12/2012 | Larocque et al. | |
| 2013/0216614 A1 * | 8/2013 | Halle | A61K 31/00 424/450 |
| 2014/0314834 A1 * | 10/2014 | Paya Cuenca | C07K 16/2887 424/450 |

FOREIGN PATENT DOCUMENTS

WO    WO 2011/150249 A1    12/2011

OTHER PUBLICATIONS

Kaczanowska et al., Journal of Leukocyte Biology, Jun. 2013, vol. 93, No. 6, pp. 847-863 (Year: 2013).*
Hennessy, et al., *Nature Reviews*, 9(4):293-307 (2010).
Mossman, et al., *Vaccine*, 23(27):3545-3554 (2005).
Schwenk, et al., *PLOS One*, 9(10):e111020-e111020 (2014).
Yu, et al., *Cancer Immunology*, 57(9):1271-1278 (2008).
Palaniyandi: "In Vitro antigastric cancer activity of squalene, a triterpenoid compound isolated from *Rhizophora mucronata* mangrove plant leaves against AGS cell line Palaniyandi T, Sivaji A, Thiruganasambandam R, Natarajan S, Hari R—Phcog Mag". Jan. 1, 2018. Retrieved from the Internet: URL:http://www.phcog.com/article.asp? ISSN=0973-1296;year=2018;volume=14;issue=57;spage=369;epage=376;aulast=Palaniyandi:type=0 [retrieved on Apr. 8, 2019]. Abstract only.

* cited by examiner

Primary Examiner — Traviss C McIntosh, III
(74) Attorney, Agent, or Firm — Robert J. Smith

(57) ABSTRACT

Disclosed is a TLR4 agonist alone or in combination with an anti-cancer agent and pharmaceutical compositions thereof, uses thereof, and methods of treatment comprising administering said composition or combination, including uses in cancer.

9 Claims, 31 Drawing Sheets

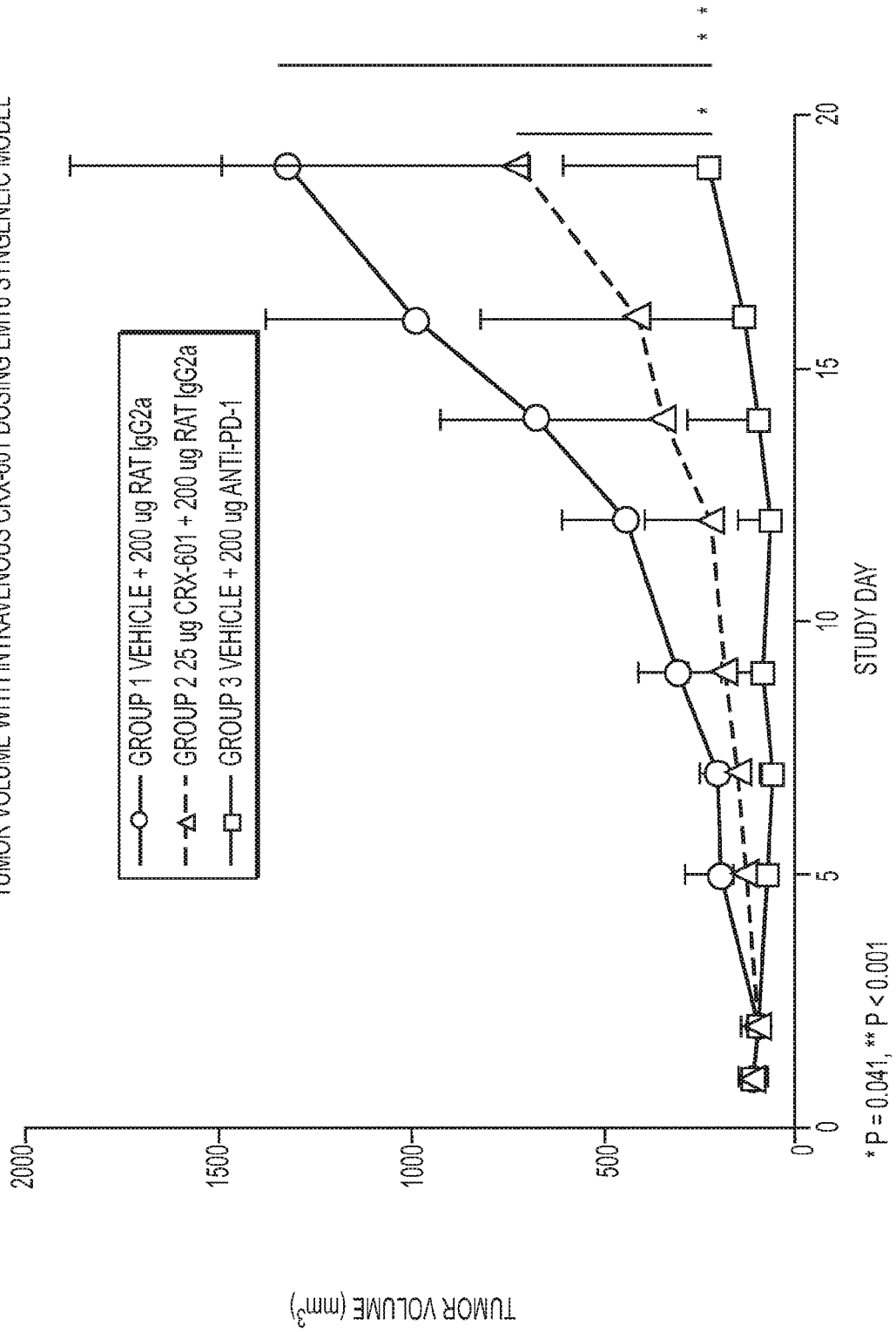

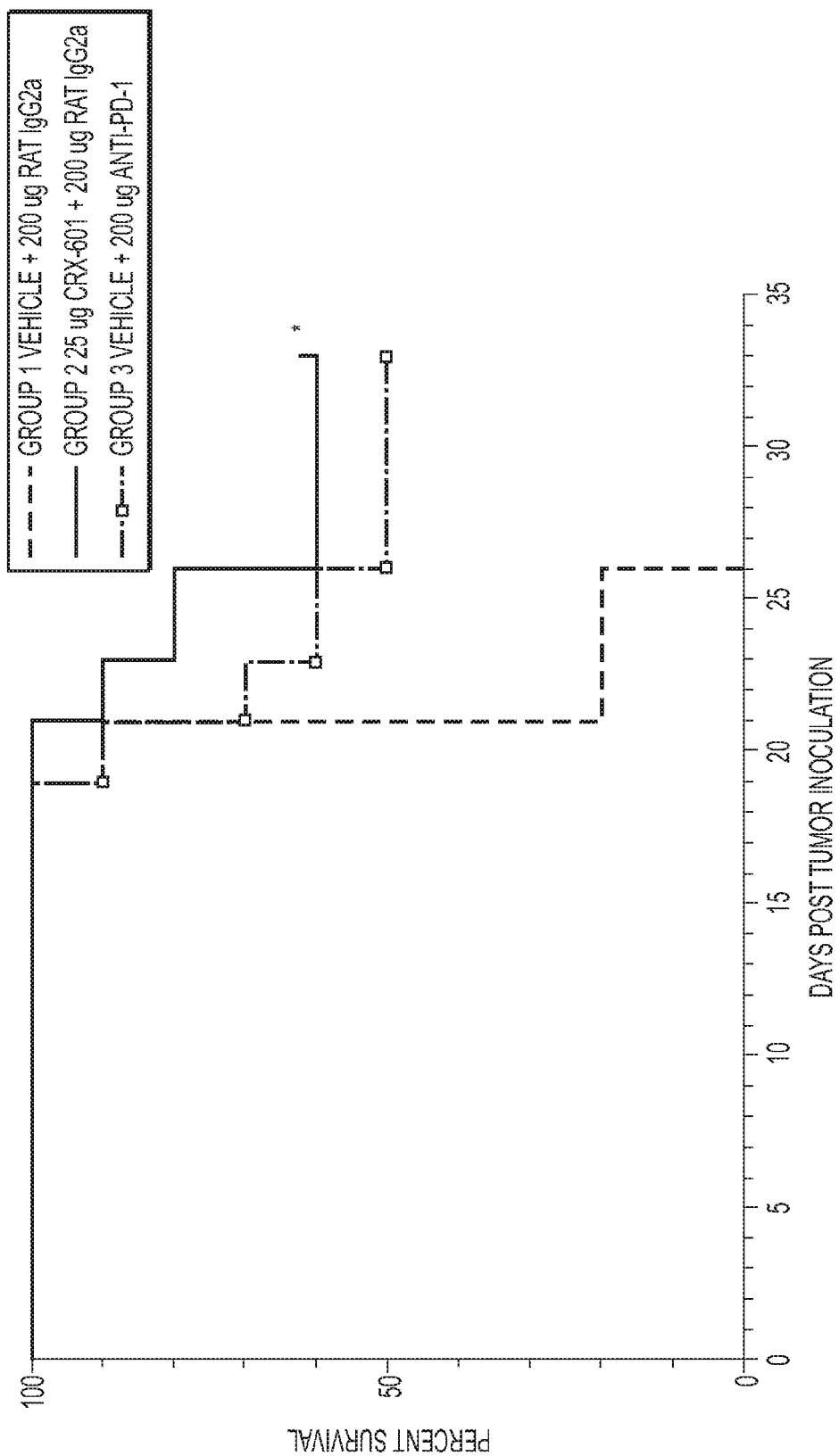

TLR4 AGONISTS AND COMPOSITIONS THEREOF AND THEIR USE IN THE TREATMENT OF CANCER

This application is a 371 of International Application No. PCT/IB2016/053290, filed Jun. 3, 2016, which claims benefit of U.S. Provisional 62/201,912, filed on Aug. 6, 2015, all of which are incorporated herein in their entireties.

FIELD OF THE INVENTION

The present invention relates to a method of treating cancer in a mammal. In particular the present invention relates to the administration of one or more TLR4 agonists alone or in combination with other anti-cancer agents.

BACKGROUND OF THE INVENTION

Effective treatment of hyperproliferative disorders including cancer is a continuing goal in the oncology field. Generally, cancer results from the deregulation of the normal processes that control cell division, differentiation and apoptotic cell death and is characterized by the proliferation of malignant cells which have the potential for unlimited growth, local expansion and systemic metastasis. Deregulation of normal processes include abnormalities in signal transduction pathways and response to factors which differ from those found in normal cells.

Immunotherapies are one approach to treat hyperproliferative disorders. A major hurdle that scientists and clinicians have encountered in the development of various types of cancer immunotherapies has been to break tolerance to self antigen (cancer) in order to mount a robust anti-tumor response leading to tumor regression. Unlike traditional development of small and large molecule agents that target the tumor, cancer immunotherapies target cells of the immune system that have the potential to generate a memory pool of effector cells to induce more durable effects and minimize recurrences.

Aminoalkyl glucosaminide phosphates (AGPs) are synthetic ligands of the Toll-like Receptor 4 (TLR4). Certain AGPs are known to be TLR4 agonists and are useful as vaccine adjuvants and for stimulating cytokine production, activating macrophages, promoting innate immune response, and augmenting antibody production in immunized animals.

Though there have been many recent advances in the treatment of cancer, there remains a need for more effective and/or enhanced treatment of an individual suffering the effects of cancer. The compositions, combinations and methods herein that relate to combining therapeutic approaches for enhancing anti-tumor immunity address this need.

SUMMARY OF THE INVENTION

Accordingly, the present invention provides TLR4 agonists, alone or in combination with anti-cancer agents and optionally in combination with other TLR4 agonists, for use in cancer therapy.

There is also provided a method of treating cancer in a human with the TLR4 agonist composition of the invention, and uses of the TLR4 agonist in combinations for therapy, preferably for therapy for cancer.

There is further provided a method for modulating the immune response of a subject in need of cancer treatment, preferably a human, comprising administering to said subject an effective amount of the TLR4 agonist alone or in combination, e.g. in one or more pharmaceutical compositions.

BRIEF DESCRIPTION OF THE DRAWINGS

FIG. 29 is a graph showing anti-tumor activity (as measured by tumor growth inhibition over time) of 25 ug/mouse of TLR4 agonist CRX-601 dosed intravenous 1×/week for 3 doses total, (*p-values=0.041, **p-value<0.001).

FIG. 30 is a graph showing survival curves of mice treated with 25 ug/mouse of TLR4 agonist CRX-601 dosed intravenous 1×/week for 3 doses total (*p-value=0.03).

DETAILED DESCRIPTION OF THE INVENTION

Compositions and Combinations

Figure 1:
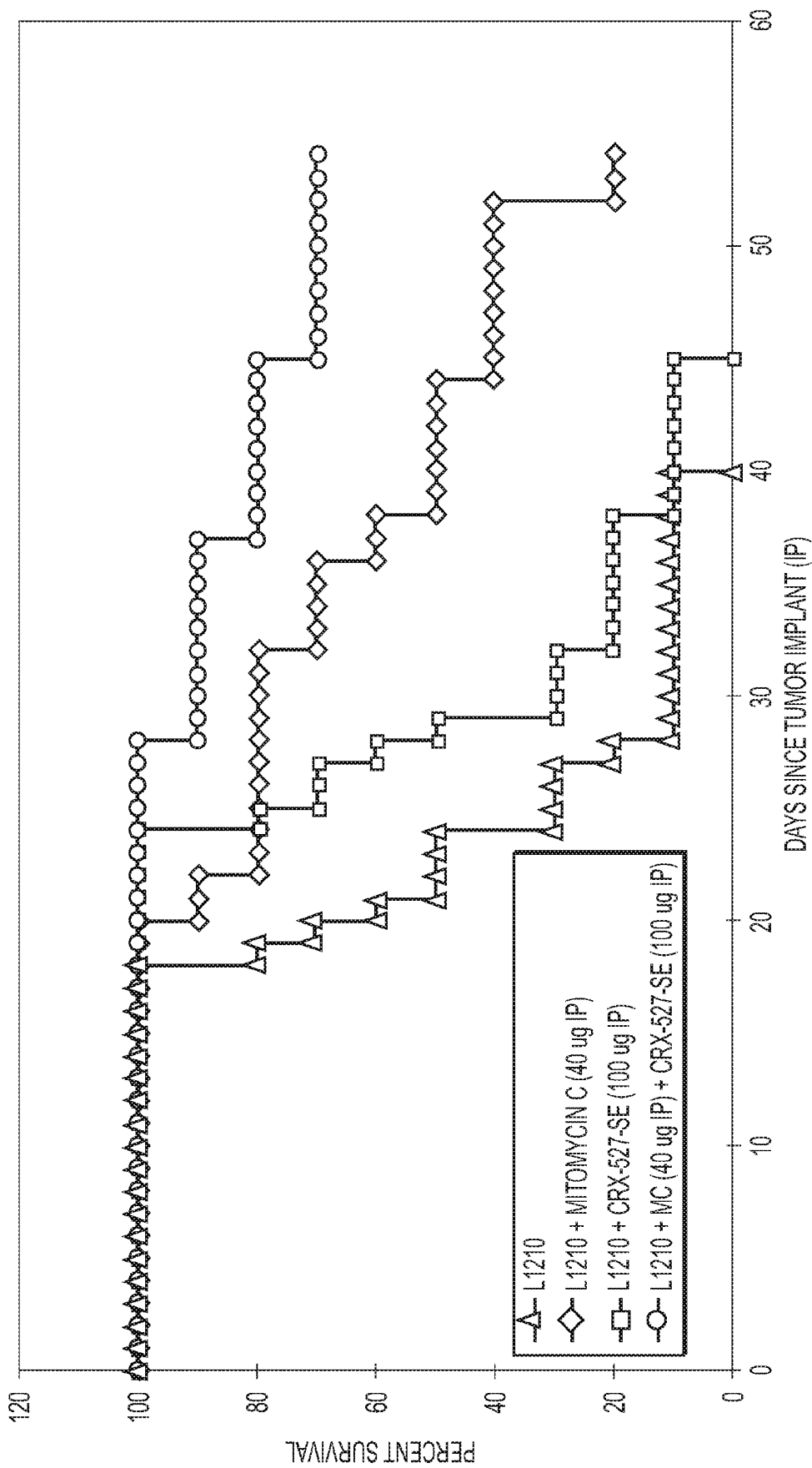
FIG. 1 is a graph showing the treatment of L1210 Murine leukemia-bearing BDF1 mice with Mitomycin-C and CRX 527.

Inducing an anti-cancer or anti-tumor effect by administration of one or more TLR4 agonists, and in particular an AGP, is an object of one embodiment of the invention. Enhancing, augmenting, improving, increasing, and otherwise changing the anti-tumor effect of an anti-cancer agent by administration of a TLR4 agonist in combination with an anti-cancer agent is an additional object of another embodiment of the invention. Described herein are TLR4 agonist compositions and combinations of a TLR4 agonist and an anti-cancer agent.

Thus, as used herein the term "combination of the invention" refers to a combination comprising a TLR4 agonist, such as an AGP, and a cancer agent each of which may be administered separately or simultaneously as described herein.

As used herein, the terms "cancer," "neoplasm," and "tumor," are used interchangeably and in either the singular or plural form, refer to cells that have undergone a malignant transformation or undergone cellular changes that result in aberrant or unregulated growth or hyperproliferation. Such changes or malignant transformations usually make such cells pathological to the host organism, thus precancers or precancerous cells that are or could become pathological and require or could benefit from intervention are also intended to be included. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient. In other words, the terms herein include cells, neoplasms, cancers, and tumors of any stage, including what a clinician refers to as precancer, tumors, in situ growths, as well as late stage metastatic growths, Tumors may be hematopoietic tumor, for example, tumors of blood cells or the like, meaning liquid tumors. Specific examples of clinical conditions based on such a tumor include leukemia such as chronic myelocytic leukemia or acute myelocytic leukemia; myeloma such as multiple myeloma; lymphoma and the like.

As used herein the term "agent" is understood to mean a substance that produces a desired effect in a tissue, system, animal, mammal, human, or other subject. Accordingly, the term "anti-cancer agent" is understood to mean a substance producing an anti-cancer effect in a tissue, system, animal, mammal, human, or other subject and likewise the term synonymous term "anti-neoplastic agent" is understood to mean a substance producing an anti-neoplastic effect in a tissue, system, animal, mammal, human, or other subject. It is also to be understood that an "agent" may be a single compound or a combination or composition of two or more compounds.

By the term "treating" and derivatives thereof as used herein, is meant therapeutic therapy. In reference to a particular condition, treating means: (1) to ameliorate the condition or one or more of the biological manifestations of the condition, (2) to interfere with (a) one or more points in the biological cascade that leads to or is responsible for the condition or (b) one or more of the biological manifestations of the condition (3) to alleviate one or more of the symptoms, effects or side effects associated with the condition or one or more of the symptoms, effects or side effects associated with the condition or treatment thereof, or (4) to slow the progression of the condition or one or more of the biological manifestations of the condition.

As used herein, "prevention" is understood to refer to the prophylactic administration of a drug to substantially diminish the likelihood or severity of a condition or biological manifestation thereof, or to delay the onset of such condition or biological manifestation thereof. The skilled artisan will appreciate that "prevention" is not an absolute term. Prophylactic therapy is appropriate, for example, when a subject is considered at high risk for developing cancer, such as when a subject has a strong family history of cancer or when a subject has been exposed to a carcinogen.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

In one embodiment the administration of a therapeutically effective amount of the combinations of the invention (or therapeutically effective amounts of each of the components of the combination) are advantageous over the individual component compounds in that the combinations provide one or more of the following improved properties when compared to the individual administration of a therapeutically effective amount of a component compound: i) a greater anti-cancer effect than the most active single agent, ii) synergistic or highly synergistic anticancer activity, iii) a dosing protocol that provides enhanced anticancer activity with reduced side effect profile, iv) a reduction in the toxic effect profile, v) an increase in the therapeutic window, or vi) an increase in the bioavailability of one or both of the component compounds.

The invention further provides pharmaceutical compositions, which include one or more of the TLR4 components referenced herein, and one or more pharmaceutically acceptable carriers, diluents, or excipients. The combination of the invention may comprise an anti-cancer agent and a TLR4 modulator, each of which may have the same or different carriers, diluents or excipients. The carrier(s), diluent(s) or excipient(s) must be acceptable in the sense of being compatible with the other ingredients of the formulation, capable of pharmaceutical formulation, and not deleterious to the recipient thereof.

The components of the combination of the invention, and pharmaceutical compositions comprising such components may be administered in any order, and in different routes; the components and pharmaceutical compositions comprising the same may be administered simultaneously.

In accordance with another aspect of the invention there is also provided a process for the preparation of a pharmaceutical composition including admixing a component of the combination of the invention and one or more pharmaceutically acceptable carriers, diluents or excipients.

The components of the invention may be administered by any appropriate route. For some components, suitable routes include oral, rectal, nasal, topical (including buccal and sublingual), vaginal, and parenteral (including subcutaneous, intramuscular, intraveneous, intradermal, intrathecal, and epidural). It will be appreciated that the preferred route may vary with, for example, the condition of the recipient of the combination and the cancer to be treated. It will also be appreciated that each of the agents administered may be administered by the same or different routes and that the components may be compounded together or in separate pharmaceutical compositions.

In one embodiment, one or more components of a combination of the invention are administered intravenously. In another embodiment, one or more components of a combination of the invention are administered intratumorally. In another embodiment, one or more components of a combination of the invention are administered systemically, e.g. intravenously, and one or more other components of a combination of the invention are administered intratumorally. In another embodiment, all of the components of a combination of the invention are administered systemically, e.g. intravenously. In an alternative embodiment, all of the components of the combination of the invention are administered intratumorally. In any of the embodiments, e.g. in this paragraph, the components of the invention are administered as one or more pharmaceutical compositions.

Antigen Binding Proteins and Antibodies

"Antigen Binding Protein (ABP)" means a protein that binds an antigen, including antibodies or engineered molecules that function in similar ways to antibodies. Such alternative antibody formats include triabody, tetrabody, miniantibody, and a minibody, Also included are alternative scaffolds in which the one or more CDRs of any molecules in accordance with the disclosure can be arranged onto a suitable non-immunoglobulin protein scaffold or skeleton, such as an affibody, a SpA scaffold, an LDL receptor class A domain, an avimer (see, e.g., U.S. Patent Application Publication Nos. 2005/0053973, 2005/0089932, 2005/0164301) or an EGF domain. An ABP also includes antigen binding fragments of such antibodies or other molecules. Further, an ABP may comprise the VH regions of the invention formatted into a full length antibody, a (Fab')2 fragment, a Fab fragment, a bi-specific or biparatopic molecule or equivalent thereof (such as scFV, bi- tri- or tetra-bodies, Tandabs etc.) when paired with an appropriate light chain. The ABP may comprise an antibody that is an IgG1, IgG2, IgG3, or IgG4; or IgM; IgA, IgE or IgD or a modified variant thereof. The constant domain of the antibody heavy chain may be selected accordingly. The light chain constant domain may be a kappa or lambda constant domain. The ABP may also be a chimeric antibody of the type described in WO86/01533 which comprises an antigen binding region and a non-immunoglobulin region.

Thus, herein an ABP of the invention or an is one that binds a receptor, and in preferred embodiments does one or more of the following; modulate signaling through receptor, modulates the function of the receptor, agonize receptor signalling, stimulate receptor function, or co-stimulate receptor signaling. One of skill in the art would readily recognize a variety of well known assays to establish such functions.

The term "antibody" as used herein refers to molecules with an antigen binding domain, and optionally an immunoglobulin-like domain or fragment thereof and includes monoclonal (for example IgG, IgM, IgA, IgD or IgE and modified variants thereof), recombinant, polyclonal, chimeric, humanized, biparatopic, bispecific and heteroconjugate antibodies, or a closed conformation multispecific antibody. An "antibody" included xenogeneic, allogeneic, syngeneic, or other modified forms thereof. An antibody may be isolated or purified. An antibody may also be recombinant, i.e. produced by recombinant means; for example, an antibody that is 90% identical to a reference antibody may be generated by mutagenesis of certain residues using recombinant molecular biology techniques known in the art. Thus, the antibodies of the present invention may comprise heavy chain variable regions and light chain variable regions of the invention which may be formatted into the structure of a natural antibody or formatted into a full length recombinant antibody, a (Fab')2 fragment, a Fab fragment, a bi-specific or biparatopic molecule or equivalent thereof (such as scFV, bi- tri- or tetra-bodies, Tandabs etc.), when paired with an appropriate light chain. The antibody may be an IgG1, IgG2, IgG3, or IgG4 or a modified variant thereof. The constant domain of the antibody heavy chain may be selected accordingly. The light chain constant domain may be a kappa or lambda constant domain. The antibody may also be a chimeric antibody of the type described in WO86/01533 which comprises an antigen binding region and a non-immunoglobulin region.

One of skill in the art will recognize that the ABPs and antibodies of the invention bind an epitope of a relevant receptor. The epitope of an ABP is the region of its antigen to which the ABP binds. Two ABPs bind to the same or overlapping epitope if each competitively inhibits (blocks) binding of the other to the antigen. That is, a 1×, 5×, 10×, 20× or 100× excess of one antibody inhibits binding of the other by at least 50% but preferably 75%, 90% or even 99% as measured in a competitive binding assay compared to a control lacking the competing antibody (see, e.g., Junghans et al., Cancer Res. 50:1495, 1990, which is incorporated herein by reference). Alternatively, two antibodies have the same epitope if essentially all amino acid mutations in the antigen that reduce or eliminate binding of one antibody reduce or eliminate binding of the other. Also the same epitope may include "overlapping epitopes" e.g. if some amino acid mutations that reduce or eliminate binding of one antibody reduce or eliminate binding of the other.

The strength of binding may be important in dosing and administration of an ABP or antibody of the invention. In one embodiment, the ABP or antibody of the invention binds to a receptor preferably a human receptor, with high affinity. For example, when measured by Biacore, the antibody binds to the receptor, with an affinity of 1-1000 nM or 500 nM or less or an affinity of 200 nM or less an affinity of 100 nM or less or an affinity of 50 nM or less or an affinity of 500 pM or less or an affinity of 400 pM or less, or 300 pM or less. In a further aspect the antibody binds to a receptor, when measured by Biacore of between about 50 nM and about 200 nM or between about 50 nM and about 150 nM, In one aspect of the present invention the antibody binds the receptor with an affinity of less than 100 nM.

In a further embodiment, binding is measured by Biacore. Affinity is the strength of binding of one molecule, e.g. an antibody of the invention, to another, e.g. its target antigen, at a single binding site. The binding affinity of an antibody to its target may be determined by equilibrium methods (e.g. enzyme-linked immunoabsorbent assay (ELISA) or radioimmunoassay (RIA)), or kinetics (e.g. BIACORE analysis). For example, the Biacore methods known in the art may be used to measure binding affinity.

Avidity is the sum total of the strength of binding of two molecules to one another at multiple sites, e.g. taking into account the valency of the interaction.

In an aspect, the equilibrium dissociation constant (KD) of the ABP or antibody and a receptor interaction is 100 nM or less, 10 nM or less, 2 nM or less or 1 nM or less. Alternatively the KD may be between 5 and 10 nM; or between 1 and 2 nM. The KD may be between 1 pM and 500 pM; or between 500 pM and 1 nM. A skilled person will appreciate that the smaller the KD numerical value, the stronger the binding. The reciprocal of KD (i.e. 1/KD) is the equilibrium association constant (KA) having units M-1. A skilled person will appreciate that the larger the KA numerical value, the stronger the binding.

The dissociation rate constant (kd) or "off-rate" describes the stability of the complex of ABP or antibody on one hand receptor on the other hand, i.e. the fraction of complexes that decay per second. For example, a kd of 0.01 s−1 equates to 1% of the complexes decaying per second. In an embodiment, the dissociation rate constant (kd) is 1×10−3 s−1 or less, 1×10−4 s−1 or less, 1×10−5 s−1 or less, or 1×10−6 s−1 or less. The kd may be between 1×10−5 s−1 and 1×10−4 s−1; or between 1×10−4 s−1 and 1×10−3 s−1.

Competition between an ABP or antibody of the invention, and a reference antibody, e.g. for binding a receptor an epitope or a fragment of the receptor, may be determined by competition ELISA, FMAT or BIAcore. In one aspect, the competition assay is carried out by Biacore. There are several possible reasons for this competition: the two proteins may bind to the same or overlapping epitopes, there may be steric inhibition of binding, or binding of the first protein may induce a conformational change in the antigen that prevents or reduces binding of the second protein.

"Binding fragments" as used herein means a portion or fragment of the ABPs or antibodies of the invention that include the antigen-binding site and are capable of binding a receptor as defined herein, e.g. but not limited to capable of binding to the same epitope of the parent or full length antibody.

Functional fragments of the ABPs and antibodies of the invention are contemplated herein.

Thus, "binding fragments" and "functional fragments" may be an Fab and F(ab')2 fragments which lack the Fc fragment of an intact antibody, clear more rapidly from the circulation, and may have less non-specific tissue binding than an intact antibody (Wahl et al., J. Nuc. Med. 24:316-325 (1983)). Also included are Fv fragments (Hochman, J. et al. (1973) Biochemistry 12:1130-1135; Sharon, J. et al. (1976) Biochemistry 15:1591-1594). These various fragments are produced using conventional techniques such as protease cleavage or chemical cleavage (see, e.g., Rousseaux et al., Meth. Enzymol., 121:663-69 (1986)).

"Functional fragments" as used herein means a portion or fragment of the ABPs or antibodies of the invention that include the antigen-binding site and are capable of binding the same target as the parent ABP or antibody, e.g. but not limited to binding the same epitope, and that also retain one or more modulating or other functions described herein or known in the art.

As the ABPs and antibodies of the present invention may comprise heavy chain variable regions and light chain variable regions of the invention which may be formatted into the structure of a natural antibody, a functional fragment is one that retains binding or one or more functions of the full length ABP or antibody as described herein. A binding fragment of an ABP or antibody of the invention may therefore comprise the VL or VH regions, a (Fab')2 fragment, a Fab fragment, a fragment of a bi-specific or biparatopic molecule or equivalent thereof (such as scFV, bi- tri- or tetra-bodies, Tandabs etc.), when paired with an appropriate light chain.

The term "CDR" as used herein, refers to the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin.

It will be apparent to those skilled in the art that there are various numbering conventions for CDR sequences; Chothia (Chothia et al. (1989) Nature 342: 877-883), Kabat (Kabat et al., Sequences of Proteins of Immunological Interest, 4th Ed., U.S. Department of Health and Human Services, National Institutes of Health (1987)), AbM (University of Bath) and Contact (University College London). The minimum overlapping region using at least two of the Kabat, Chothia, AbM and contact methods can be determined to provide the "minimum binding unit". The minimum binding unit may be a subportion of a CDR. The structure and protein folding of the antibody may mean that other residues are considered part of the CDR sequence and would be understood to be so by a skilled person. It is noted that some of the CDR definitions may vary depending on the individual publication used.

Unless otherwise stated and/or in absence of a specifically identified sequence, references herein to "CDR", "CDRL1", "CDRL2", "CDRL3", "CDRH1", "CDRH2", "CDRH3" refer to amino acid sequences numbered according to any of the known conventions; alternatively, the CDRs are referred to as "CDR1," "CDR2," "CDR3" of the variable light chain and "CDR1," "CDR2," and "CDR3" of the variable heavy chain. In particular embodiments, the numbering convention is the Kabat convention.

The term "CDR variant" as used herein, refers to a CDR that has been modified by at least one, for example 1, 2 or 3, amino acid substitution(s), deletion(s) or addition(s), wherein the modified antigen binding protein comprising the CDR variant substantially retains the biological characteristics of the antigen binding protein pre-modification. It will be appreciated that each CDR that can be modified may be modified alone or in combination with another CDR. In one aspect, the modification is a substitution, particularly a conservative substitution, for example as shown in Table 1.

TABLE 1

| Side chain | Members |
|---|---|
| Hydrophobic | Met, Ala, Val, Leu, Ile |
| Neutral hydrophilic | Cys, Ser, Thr |
| Acidic | Asp, Glu |
| Basic | Asn, Gln, His, Lys, Arg |
| Residues that influence chain orientation | Gly, Pro |
| Aromatic | Trp, Tyr, Phe |

For example, in a variant CDR, the amino acid residues of the minimum binding unit may remain the same, but the flanking residues that comprise the CDR as part of the Kabat or Chothia definition(s) may be substituted with a conservative amino acid residue.

Such antigen binding proteins comprising modified CDRs or minimum binding units as described above may be referred to herein as "functional CDR variants" or "functional binding unit variants".

The antibody may be of any species, or modified to be suitable to administer to a cross species. For example the CDRs from a mouse antibody may be humanized for administration to humans. In any embodiment, the antigen binding protein is optionally a humanized antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., Proc. Natl Acad Sci USA, 86:10029-10032 (1989), Hodgson et al., Bio/Technology, 9:421 (1991)). A suitable human acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanised antibodies—see for example EP-A-0239400 and EP-A-054951.

In yet a further embodiment, the humanized antibody has a human antibody constant region that is an IgG. In another embodiment, the IgG is a sequence as disclosed in any of the above references or patent publications.

For nucleotide and amino acid sequences, the term "identical" or "identity" indicates the degree of identity between two nucleic acid or two amino acid sequences when optimally aligned and compared with appropriate insertions or deletions.

The percent identity between two sequences is a function of the number of identical positions shared by the sequences (i.e., % identity=number of identical positions/total number of positions multiplied by 100), taking into account the number of gaps, and the length of each gap, which need to be introduced for optimal alignment of the two sequences. The comparison of sequences and determination of percent identity between two sequences can be accomplished using a mathematical algorithm, as described below.

Percent identity between a query nucleic acid sequence and a subject nucleic acid sequence is the "Identities" value, expressed as a percentage, which is calculated by the BLASTN algorithm when a subject nucleic acid sequence has 100% query coverage with a query nucleic acid sequence after a pair-wise BLASTN alignment is performed. Such pair-wise BLASTN alignments between a query nucleic acid sequence and a subject nucleic acid sequence are performed by using the default settings of the BLASTN algorithm available on the National Center for Biotechnology Institute's website with the filter for low complexity regions turned off. Importantly, a query nucleic acid sequence may be described by a nucleic acid sequence identified in one or more claims herein.

Percent identity between a query amino acid sequence and a subject amino acid sequence is the "Identities" value, expressed as a percentage, which is calculated by the BLASTP algorithm when a subject amino acid sequence has 100% query coverage with a query amino acid sequence after a pair-wise BLASTP alignment is performed. Such pair-wise BLASTP alignments between a query amino acid sequence and a subject amino acid sequence are performed by using the default settings of the BLASTP algorithm available on the National Center for Biotechnology Institute's website with the filter for low complexity regions turned off. Importantly, a query amino acid sequence may be described by an amino acid sequence identified in one or more claims herein.

In any embodiment of the invention herein, the ABP or antibody may have any one or all CDRs, VH, VL, with 99, 98, 97, 96, 95, 94, 93, 92, 91, or 90 percent identity to the sequence shown or referenced, e.g. as defined by a SEQ ID NO.

TLR-4 Agonists

The combinations of the invention comprise TLR-4 agonists, that is molecules that activate TLR4, for example by binding and initiating conformational changes or signaling by engaging TLR4.

Preferred TLR-4 agonists are aminoalkyl glucosaminide phosphate compounds (AGPs). Toll-like receptor 4 recognizes bacterial LPS (lipopolysaccharide) and when activated initiates an innate immune response. AGPs are a monosaccharide mimetic of the lipid A protein of bacterial LPS and have been developed with ether and ester linkages on the "acyl chains" of the compound. Processes for making these compounds are known and disclosed, for example, in WO 2006/016997, U.S. Pat. Nos. 7,288,640 and 6,113,918, and WO 01/90129, which are hereby incorporated by reference in their entireties. Other AGPs and related processes are disclosed in U.S. Pat. Nos. 7,129,219, 6,525,028 and 6,911,434. AGPs with ether linkages on the acyl chains employed in the composition of the invention are known and disclosed in WO 2006/016997 which is hereby incorporated by reference in its entirety. Of particular interest, are the aminoalkyl glucosaminide phosphate compounds set forth and described according to Formula (III) at paragraphs [0019] through [0021] in WO 2006/016997.

Aminoalkyl glucosaminide phosphate compounds employed in the present invention have the structure set forth in Formula 1 as follows:

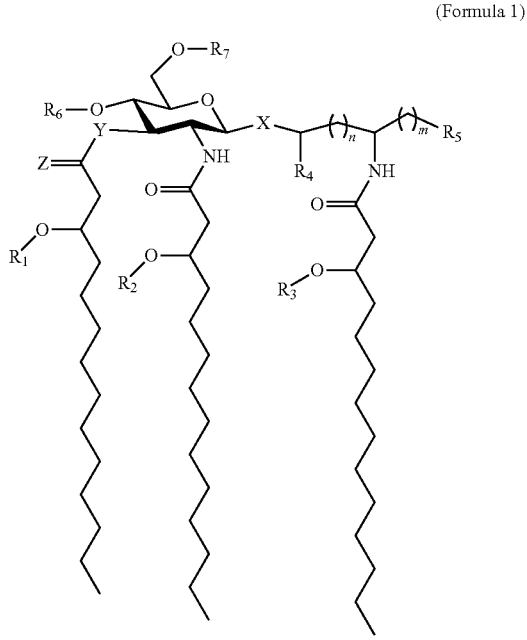

(Formula 1)

wherein
m is 0 to 6
n is 0 to 4;
X is O or S, preferably O;
Y is O or NH;
Z is O or H;
each R1, R2, R3 is selected independently from the group consisting of a C7-20 acyl and a C1-20 alkyl;
R4 is H or Me;
R5 is selected independently from the group consisting of —H, —OH, —(C1-C4) alkoxy, —PO3R8R9, —OPO3R8R9, —SO3R8, —OSO3R8, —NR8R9, SR8, —CN, —NO2, —CHO, —CO2R8, and —CONR8R9, wherein R8 and R9 are each independently selected from H and (C1-C4) alkyl; and
each R6 and R7 is independently H or PO3H2.

In Formula 1 the configuration of the 3' stereogenic centers to which the normal fatty acyl residues (that is, the secondary acyloxy or alkoxy residues, e.g., R1O, R2O, and R3O) are attached is R or S, preferably R (as designated by Cahn-Ingold-Prelog priority rules). Configuration of aglycon stereogenic centers to which R4 and R5 are attached can be R or S. All stereoisomers, both enantiomers and diastereomers, and mixtures thereof, are considered to fall within the scope of the present invention.

The number of carbon atoms between heteroatom X and the aglycon nitrogen atom is determined by the variable "n", which can be an integer from 0 to 4, preferably an integer from 0 to 2.

The chain length of normal fatty acids R1, R2, and R3 can be from about 7 to about 16 carbons, preferably from about 9 to about 14 carbons. The chain lengths can be the same or different. Some preferred embodiments include chain lengths where R1, R2 and R3 are 10 or 12 or 14.

Formula 1 encompasses L/D-seryl, -threonyl, -cysteinyl ether and ester lipid AGPs, both agonists and their homologs (n=1-4), as well as various carboxylic acid bioisosteres (i.e, R5 is an acidic group capable of salt formation; the phosphate can be either on 4- or 6-position of the glucosamine unit, but preferably is in the 4-position).

In a preferred embodiment of the invention employing an AGP compound of Formula 1, n is 0, R5 is CO2H, R6 is PO3H2, and R7 is H. This preferred AGP compound is set forth as the structure in Formula 1a as follows:

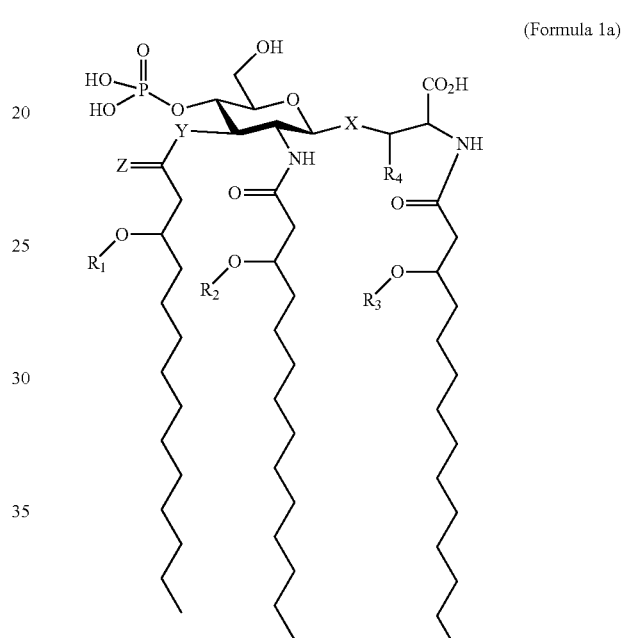

(Formula 1a)

wherein X is O or S; Y is O or NH; Z is O or H; each R1, R2, R3 is selected independently from the group consisting of a C7-20 acyl and a C7-20 alkyl; and R4 is H or methyl.

In Formula 1a the configuration of the 3' stereogenic centers to which the normal fatty acyl residues (that is, the secondary acyloxy or alkoxy residues, e.g., R1O, R2O, and R3O) are attached as R or S, preferably R (as designated by Cahn-Ingold-Prelog priority rules). Configuration of aglycon stereogenic centers to which R4 and CO2H are attached can be R or S. All stereoisomers, both enantiomers and diastereomers, and mixtures thereof, are considered to fall within the scope of the present invention.

Formula 1a encompasses L/D-seryl, -threonyl, -cysteinyl ether or ester lipid AGPs agonists.

In both Formula 1 and Formula 1a, Z is O attached by a double bond or two hydrogen atoms which are each attached by a single bond. That is, the compound is ester-linked when Z=Y=O; amide-linked when Z=O and Y=NH; and ether-linked when Z=H/H and Y=O.

Especially preferred compounds of Formula 1 are referred to as CRX-601 and CRX-527. Their structures are set forth as follows:

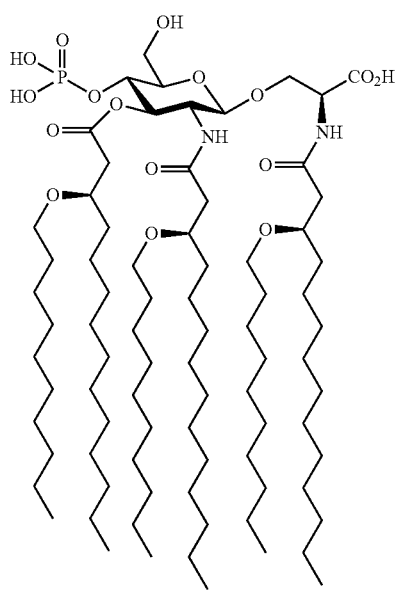

(CRX-601)

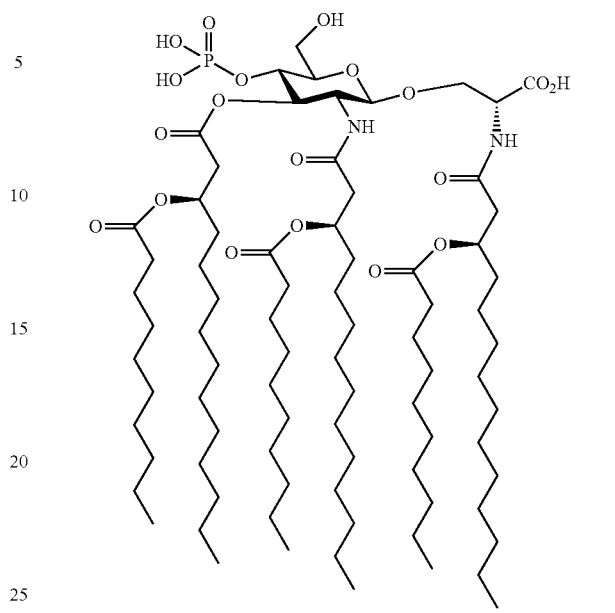

CRX-547

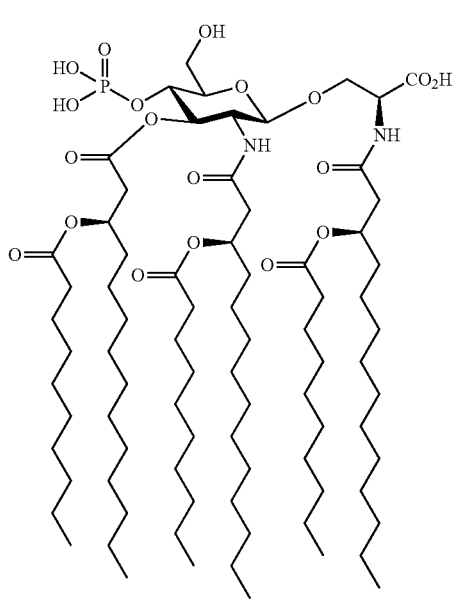

(CRX-527)

Additionally, another preferred embodiment employs CRX-547 having the structure shown.

AGP Buffers

In one embodiment of the present invention, the composition comprising a TLR4agonist, preferably an AGP, is buffered using a zwitterionoic buffer. Suitably, the zwitterionic buffer is an aminoalkanesulfonic acid or suitable salt. Examples of amninoalkanesulfonic buffers include but are not limlited to HEPES, HEPPS/EPPS, MOPS, MOBS and PIPES. Preferably, the buffer is a pharmaceutically acceptable buffer, suitable for use in humans, such as in for use in a commercial injection product. Most preferably the buffer is HEPES.

Methods of Treatment

The compositions and combinations of the invention are believed to have utility in disorders wherein the engagement of TLR4, is beneficial.

The present invention thus also provides a composition or combination of the invention, for use in therapy, particularly in the treatment of disorders wherein the engagement of TLR4, is beneficial, particularly cancer.

A further aspect of the invention provides a method of treatment of a disorder wherein engagement of TLR4 is beneficial, comprising administering a combination of the invention.

A further aspect of the present invention provides the use of a combination of the invention in the manufacture of a medicament for the treatment of a disorder engagement of TLR4 is beneficial. In preferred embodiments the disorder is cancer.

Examples of cancers that are suitable for treatment with combination of the invention include, but are limited to, both primary and metastatic forms of head and neck, breast, lung, colon, ovary, and prostate cancers. Suitably the cancer is selected from: brain (gliomas), glioblastomas, astrocytomas, glioblastoma multiforme, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid, lymphoblastic T cell leukemia, Chronic myelogenous leukemia, Chronic lymphocytic leukemia, Hairy-cell leukemia, acute lymphoblastic leukemia, acute myelogenous leukemia, AML, Chronic neutrophilic leukemia, Acute lymphoblastic T cell leukemia, plasmacytoma, Immunoblastic large cell leukemia, Mantle cell leukemia, Multiple myeloma Megakaryoblastic leukemia, multiple myeloma, acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

Additionally, examples of a cancer to be treated include Barret's adenocarcinoma; billiary tract carcinomas; breast cancer; cervical cancer; cholangiocarcinoma; central nervous system tumors including primary CNS tumors such as glioblastomas, astrocytomas (e.g., glioblastoma multiforme) and ependymomas, and secondary CNS tumors (i.e., metastases to the central nervous system of tumors originating outside of the central nervous system); colorectal cancer including large intestinal colon carcinoma; gastric cancer; carcinoma of the head and neck including squamous cell carcinoma of the head and neck; hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia; hepatocellular carcinoma; lung cancer including small cell lung cancer and non-small cell lung cancer; ovarian cancer; endometrial cancer; pancreatic cancer; pituitary adenoma; prostate cancer; renal cancer; sarcoma; skin cancers including melanomas; and thyroid cancers.

Suitably, the present invention relates to a method for treating or lessening the severity of a cancer selected from: brain (gliomas), glioblastomas, astrocytomas, glioblastoma multiforme, Bannayan-Zonana syndrome, Cowden disease, Lhermitte-Duclos disease, breast, colon, head and neck, kidney, lung, liver, melanoma, ovarian, pancreatic, prostate, sarcoma and thyroid.

Suitably, the present invention relates to a method for treating or lessening the severity of a cancer selected from ovarian, breast, pancreatic and prostate.

Suitably the present invention relates to a method for treating or lessening the severity of pre-cancerous syndromes in a mammal, including a human, wherein the pre-cancerous syndrome is selected from: cervical intraepithelial neoplasia, monoclonal gammapathy of unknown significance (MGUS), myelodysplastic, syndrome, aplastic anemia, cervical lesions, skin nevi (pre-melanoma), prostatic intraepithleial (intraductal) neoplasia (PIN), Ductal Carcinoma in situ (DCIS), colon polyps and severe hepatitis or cirrhosis.

The combination of the invention may be used alone or in combination with one or more other therapeutic agents. The invention thus provides in a further aspect a further combination comprising a combination of the invention with a further therapeutic agent or agents, compositions and medicaments comprising the combination and use of the further combination, compositions and medicaments in therapy, in particular in the treatment of diseases susceptible engagement of TLR4.

In the embodiment, the combination of the invention may be employed with other therapeutic methods of cancer treatment. In particular, in anti-neoplastic therapy, combination therapy with other chemotherapeutic, hormonal, antibody agents as well as surgical and/or radiation treatments other than those mentioned above are envisaged. Combination therapies according to the present invention thus include the administration of a TLR4 agonist as well as optional use of other therapeutic agents including other anti-neoplastic agents. Such combination of agents may be administered together or separately and, when administered separately this may occur simultaneously or sequentially in any order, both close and remote in time. In one embodiment, the pharmaceutical combination includes a TLR4 agonist, and optionally at least one additional anti-neoplastic agent, In one embodiment, the further anti-cancer therapy is surgical and/or radiotherapy.

In one embodiment, the further anti-cancer therapy is at least one additional anti-neoplastic agent.

Any anti-neoplastic agent that has activity versus a susceptible tumor being treated may be utilized in the combination. Typical anti-neoplastic agents useful include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine angiogenesis inhibitors; immunotherapeutic agents; proapoptotic agents; and cell cycle signaling inhibitors.

Anti-microtubule or anti-mitotic agents: Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids, Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree Taxus brevifolia and is commercially available as an injectable solution TAXOL®. It is a member of the taxane family of terpenes. Paclitaxel has been approved for clinical use in the treatment of refractory ovarian cancer in the United States (Markman et al., Yale Journal of Biology and Medicine, 64:583, 1991; McGuire et al., Ann. Intern, Med., 111:273, 1989) and for the treatment of breast cancer (Holmes et al., J. Nat. Cancer Inst., 83; 1797,1991.) It is a potential candidate for treatment of neoplasms in the skin (Einzig et. al., Proc. Am. Soc. Olin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine, N-tert-butyl ester, 13-ester with 5β-20-epoxy-1,2α, 4,7β, 10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes: Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, oxaliplatin, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer.

Carboplatin, platinum, diammine [1,1-cyclobutane-dicarboxylate(2)-O,O'], is commercially available as PARAPLATIN® as an injectable solution. Carboplatin is primarily indicated in the first and second line treatment of advanced ovarian carcinoma.

Alkylating agents: Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias.

Melphalan, 4-[bis(2-chloroethypamino-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease.

Busulfan, 1,4-butanediol dimethanesulfonate, is commercially available as MYLERAN® TABLETS. Busulfan is indicated for the palliative treatment of chronic myelogenous leukemia. Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease.

Antibiotic anti-neoplastics; Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas.

Topoisomerase II inhibitors: Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children.

Antimetabolite neoplastic agents: Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine).

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Other purine analogs include pentostatin, erythrohydroxynonyladenine, fludarabine phosphate, and cladribine.

Gemcitabine, 2'-deoxy-2', 2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer.

Methotrexate, N[4[[(2,4-diamino-6-pteridinyl) methyl]methylamino] benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder.

Topoisomerase I inhibitors: Camptothecins, including, camptothecin and camptothecin derivatives are available or under development as Topoisomerase I inhibitors, Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®. Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I: DNA: irintecan or SN-38 ternary complex with replication enzymes. lrinotecan is indicated for treatment of metastatic cancer of the colon or rectum.

Topotecan HCl, (S)-10-[(dimethylarnino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of carnptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer.

Hormones and hormonal analogues: Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxylene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal transduction pathway inhibitors: Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3 domain blockers, serine/threonine kinases, phosphatidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, ret, vascular endothelial growth factor receptor (VEGFr), tyrosine kinase with immunoglobulin-like and epidermal growth factor identity domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 February 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L., (1995), Cancer Treatment and Research. 78: 3-27, Lackey, K. et al Bioorganic and Medicinal Chemistry Letters, (10), 2000, 223-226; U.S. Pat. No. 6,268,391; and Martinez-lacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8: Ashby, M. N. (1998), Current Opinion in Lipidology. 9 (2) 99-102; and BioChim, Biophys. Acta, (19899)1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kinases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Anti-angiogenic agents: Anti-angiogenic agents including non-receptorMEKngiogenesis inhibitors may alo be useful. Anti-angiogenic agents such as those which inhibit the effects of vascular edothelial growth factor, (for example the anti-vascular endothelial cell growth factor antibody bevacizumab [Avastin™], and compounds that work by other mechanisms (for example linomide, inhibitors of integrin αvβ3 function, endostatin and angiostatin);

Immunotherapeutic agents: Agents used in immunotherapeutic regimens may also be useful in combination with the compounds of formula (I). Immunotherapy approaches, including for example ex-vivo and in-vivo approaches to increase the immunogenecity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies Proapoptotoc agents: Agents used in proapoptotic regimens (e.g., bcl-2 antisense oligonucleotides) may also be used in the combination of the present invention.

Cell cycle signalling inhibitors: Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the combination of the present invention comprises a TLR4 agonist and at least one anti-neoplastic agent selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine MEKngiogenesis inhibitors, immunotherapeutic agents, proapoptotic agents, and cell cycle signaling inhibitors.

In one embodiment, the combination of the present invention comprises a TLR4 agonist and at least one anti-neoplastic agent which is an anti-microtubule agent selected from diterpenoids and vinca alkaloids.

In a further embodiment, the at least one anti-neoplastic agent agent is a diterpenoid.

In a further embodiment, the at least one anti-neoplastic agent is a vinca alkaloid.

In one embodiment, the combination of the present invention a TLR4 agonist and a east one anti-neoplastic agent, which is a platinum coordination complex.

In a further embodiment, the at least one anti-neoplastic agent is paclitaxel, carboplatin, or vinorelbine.

In a further embodiment, the at east one anti-neoplastic agent is carboplatin.

In a further embodiment, the at least one anti-neoplastic agent is vinorelbine.

In a further embodiment, the at least one anti-neoplastic agent is paclitaxel.

In one embodiment, the combination of the present invention comprises a TLR4 agonist and at least one anti-neoplastic agent which is a signal transduction pathway inhibitor.

In a further embodiment the signal transduction pathway inhibitor is an inhibitor of a growth factor receptor kinase VEGFR2, TIE2, PDGFR, BTK, erbB2, EGFr, IGFR-1, TrkA, TrkB, TrkC, or c-fms.

In a further embodiment the signal transduction pathway inhibitor is an inhibitor of a serine/threonine kinase rafk, akt, or PKC-zeta.

In a further embodiment the signal transduction pathway inhibitor is an inhibitor of a non-receptor tyrosine kinase selected from the src family of kinases.

In a further embodiment the signal transduction pathway inhibitor is an inhibitor of c-src.

In a further embodiment the signal transduction pathway inhibitor is an inhibitor of Ras oncogene selected from inhibitors of farnesyl transferase and geranylgeranyl transferase.

In a further embodiment the signal transduction pathway inhibitor is an inhibitor of a serine/threonine kinase selected from the group consisting of PI3K.

In a further embodiment the signal transduction pathway inhibitor is a dual EGFr/erbB2 inhibitor, for example N-{3-Chloro-4-[(3-fluorobenzyl) oxy]phenyl}-6-[5-({[2-(methanesulphonyl) ethyl]amino}methyl)-2-furyl]-4-quinazolinamine (structure below):

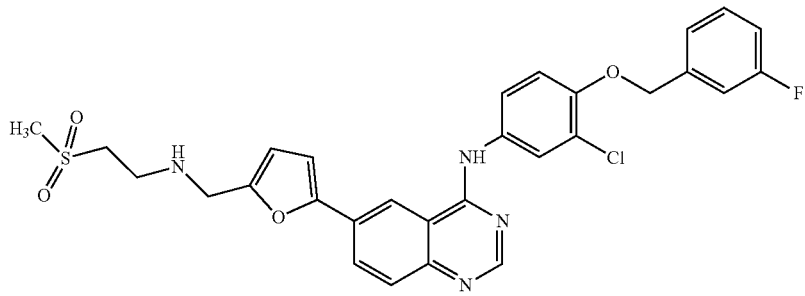 [SMILES: CS(=O)(=O)CCNCc1ccc(-c2ccc3ncnc(Nc4ccc(OCc5cccc(F)c5)c(Cl)c4)c3c2)o1]

In one embodiment, the combination of the present invention comprises a compound of formula I or a salt or solvate thereof and at least one anti-neoplastic agent which is a cell cycle signaling inhibitor.

In further embodiment, cell cycle signaling inhibitor is an inhibitor of CDK2, CDK4 or CDK6.

In one embodiment the mammal in the methods and uses of the present invention is a human.

As indicated, therapeutically effective amounts of the combinations of the invention (an anti-cancer agent and a TLR4 agonist) are administered to a human. Typically, the therapeutically effective amount of the administered agents of the present invention will depend upon a number of factors including, for example, the age and weight of the subject, the precise condition requiring treatment, the severity of the condition, the nature of the formulation, and the route of administration. Ultimately, the therapeutically effective amount will be at the discretion of the attendant physician.

The following examples are intended for illustration only and are not intended to limit the scope of the invention in any way.

EXAMPLES

NON-LIMITING EXAMPLES The combination of chemotherapy and AGP treatment results in significant enhancement of survival in murine cancer models (compared to chemotherapy or AGP alone). Evidence for synergy between CRX-527 and chemotherapy is seen in following systems: Murine Leukemia model (L1210), Murine Ovarian Teratoma model (MOT), Murine Melanoma model (B16), Breast Cancer (4T1).

Example 1 L120 Murine Leukemia Model: Combination of Chemotherapy and Immunomodulation Improves Anti-Cancer Response To investigate whether a combination treatment consisting of the chemotherapeutic mitomycin C and the AGP CRX-527 would prolong survival of cancer-bearing mice better than either treatment alone, BDF1 mice (10 per group) that had been seeded with L1210 murine leukemia cells ($10^4$ tumor cells via the intraperitoneal (IP) route) on day 0 were treated with, 1) nothing (untreated control), 2) an intraperitoneal injection of mitomycin C (40 ug) on day 6, 3) an IP injection of CRX-527-AF (100 ug CRX-527 in Aqueous Formulation (AF), which is 0.02% dipalmitoyl phosphatidyl choline in water) on day 7, or 4) an IP injection of mitomycin C on day 6 followed by an IP injection of CRX-527-AF on day 7. Survival curves through day 54 are presented for each group in FIG. 1. Mice administered both mitomycin C and CRX-527 had significantly prolonged survival compared to mice administered either component alone.

Example 2 Mouse Ovarian Tumor (MOT) Model

Timing of Administration of Chemotherapy and Immunomodulator

Figure 2:
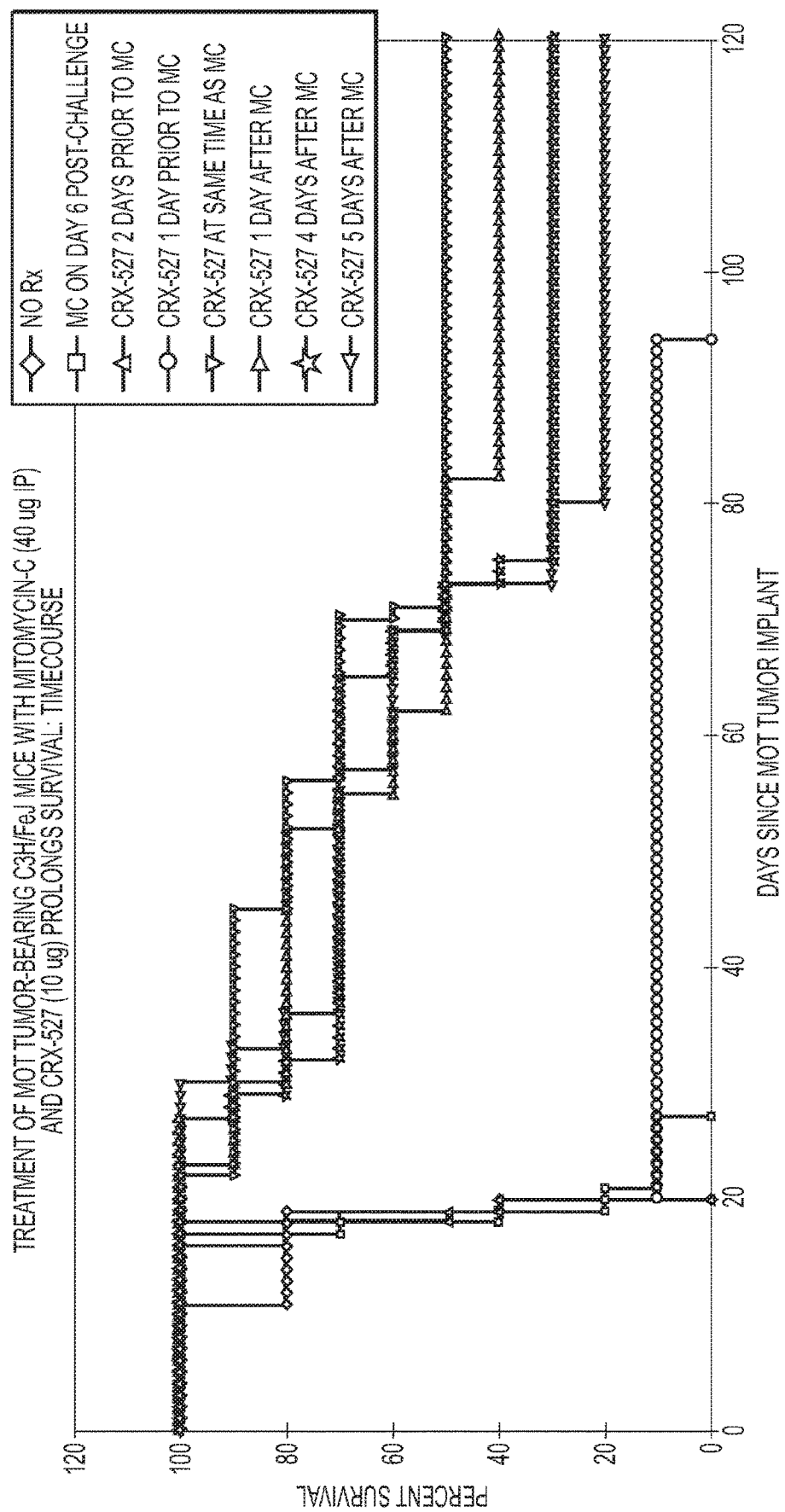
FIG. 2 is a graph showing the treatment of MOT tumor-bearing CeH/FeJ mice with Mitomycin-C.

Mice administered both mitomycin C and CRX-527 also demonstrated significantly prolonged survival compared to mice administered either component alone in the Mouse Ovarian Tumor (MOT) model. To determine whether the timing of administration of the chemotherapeutic and TLR4 ligand is important for the anti-cancer response, C3H/FeJ mice (10 per group) seeded with Mouse Ovarian Tumor (MOT) cells ($10^4$ tumor cells via the IP route) on day 0 were treated with, 1) nothing (untreated control), 2) mitomycin C (40 ug) on day 6, 3) CRX-527-SE (10 ug in a Stable Emulsion formulation containing 2% squalene oil-in-water) on day 4 followed by mitomycin C on day 6, 4) CRX-527-SE on day 5 followed by mitomycin C on day 6, 5) both CRX-527-SE and mitomycin C on day 6, 6) mitomycin C on day 6 followed by CRX-527-SE on day 7, 7) mitomycin C on day 6 followed by CRX-527-SE on day 10, and 8) mitomycin C on day 6 followed by CRX-527-SE on day 11. The dose/route for mitomycin C and CRX-527-SE administration was always 40 ug IP and 10 ug IP, respectively. The groups administered CRX-527 at the same time as or up to 5 days after mitomycin C had significantly prolonged survival times compared to the groups that received nothing (untreated control), mitomycin alone or CRX527-SE followed by mitomycin C (FIG. 2), indicating that the benefit of combination therapy in this cancer model is observed when an effective TLR4 ligand such as CRX-527 is administered at the same time as or after a chemotherapy agent such as mitomycin C.

Example 3 TLR4 Dependence

Figure 3:
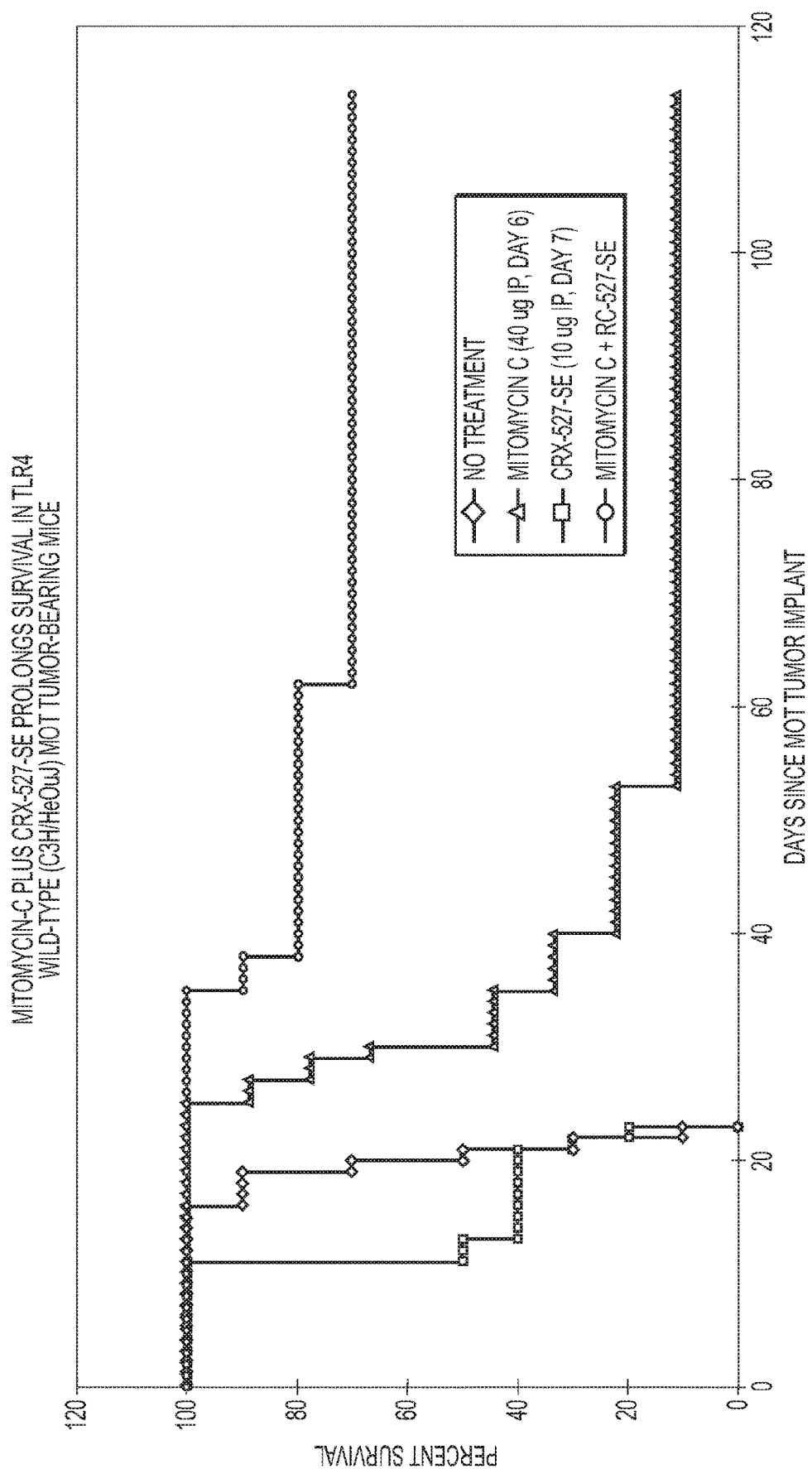
FIG. 3 is a graph showing Mitomycin-C and CRX-527 in wild-type MOT tumor-bearing mice.
Figure 4:
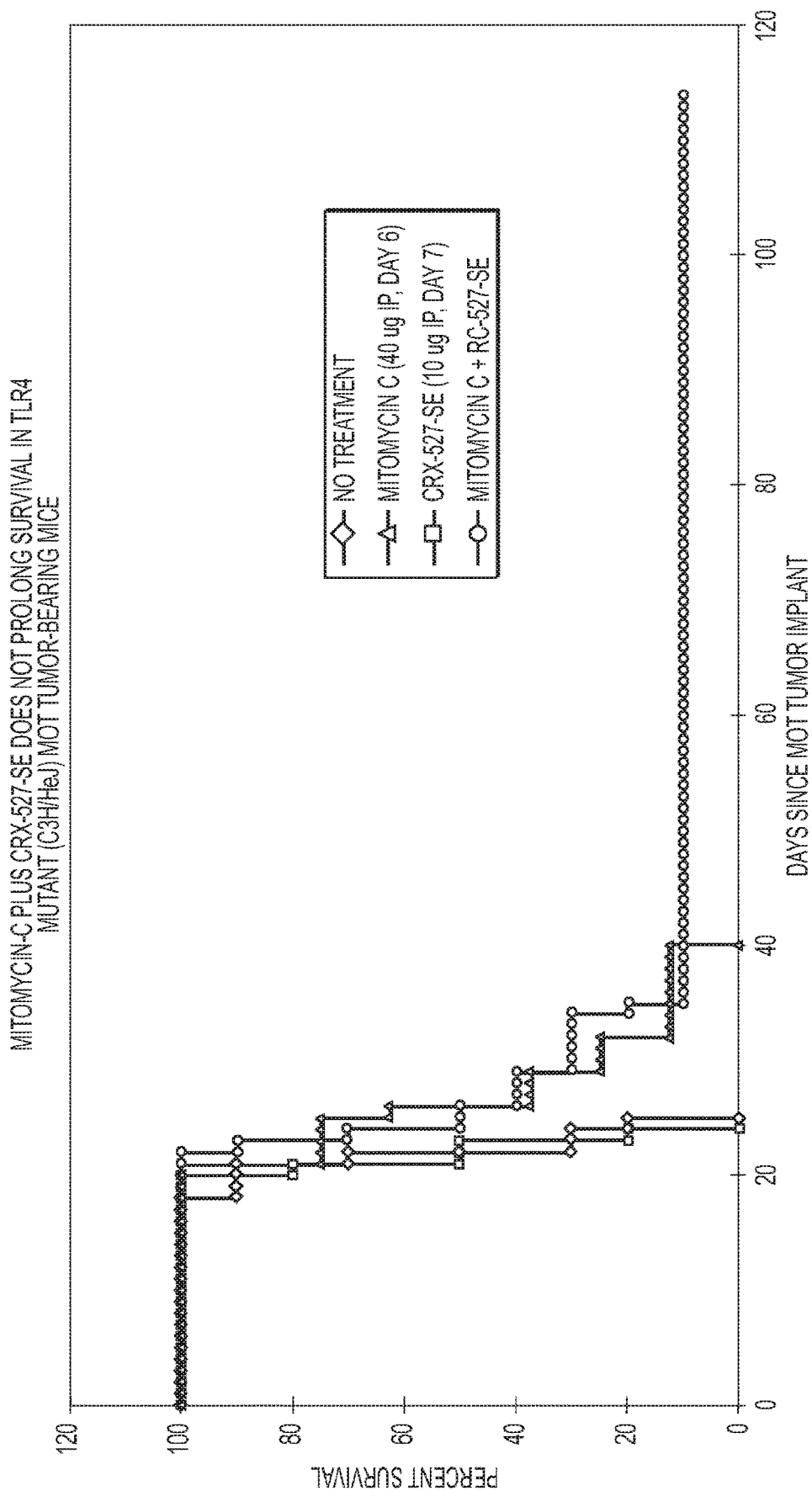
FIG. 4 is a graph showing Mitomycin-C and CRX-527 in TLR4 mutant MOT tumor-bearing mice.

C3H/HeJ mice have a mutation in the gene coding for toll-like receptor 4 (TLR4) and, as a result, do not respond to TLR4 ligands such as lipopolysaccharide (LPS) or AGPs such as CRX-527. We utilized these TLR4 non-responder mice (10 per group) to show that the anti-cancer activity elicited by CRX-527 in wild-type mice is dependent on the presence of functional TLR4. As expected, CRX-527 promoted survival in C3H/HeOuJ wild-type mice when administered alone or in combination with mitomycin C (FIG. 3), but did not promote survival in MOT-bearing C3H/HeJ mice (FIG. 4).

Example 4 Formulation

Figure 5:
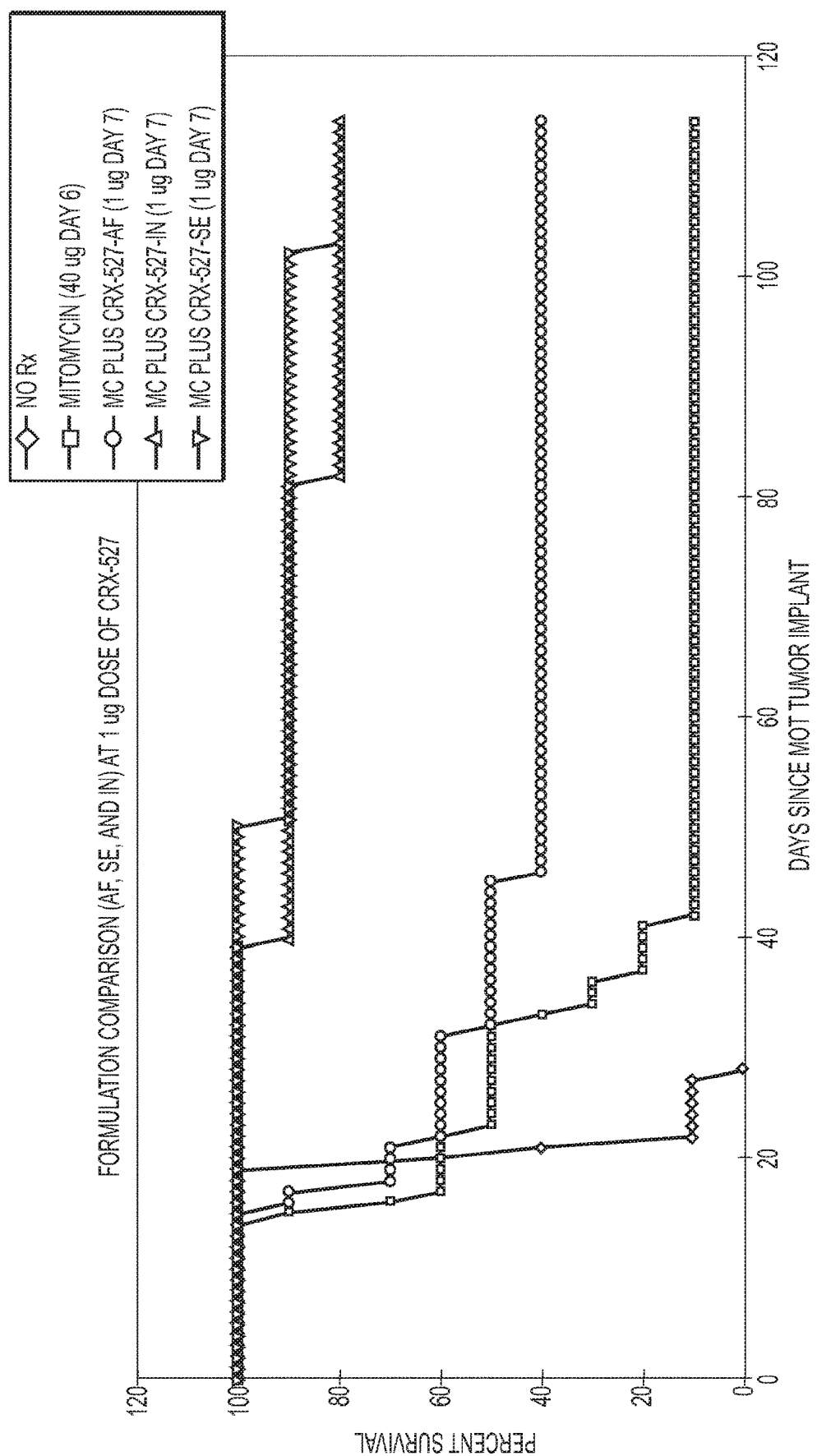
FIG. 5 is a graph showing a comparison of aqueous, intranasal and submicron emulsion 1 ug 10 ug formulations of CRX 527.
Figure 6:
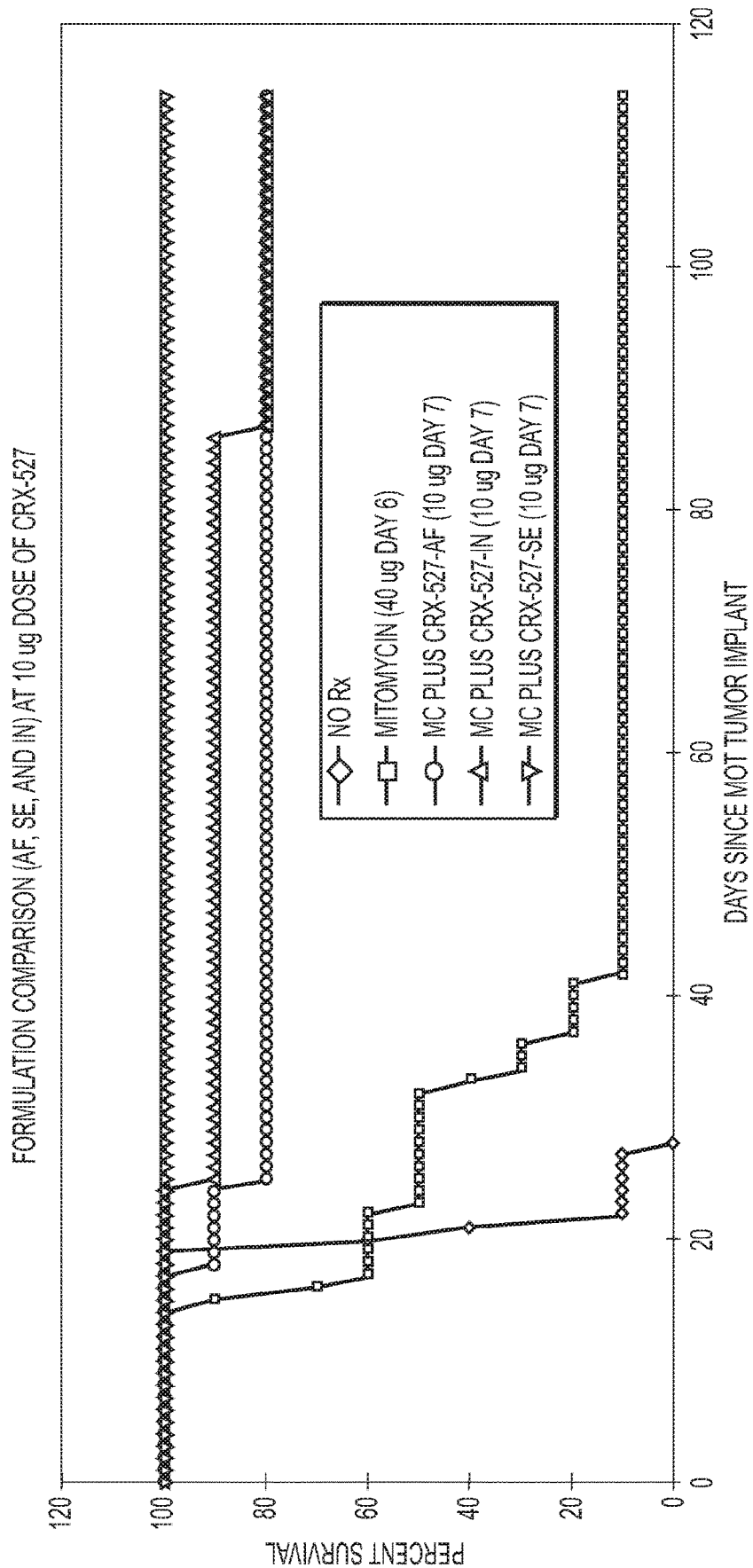
FIG. 6 is a graph showing a comparison of aqueous, IN and submicron emulsion formulations of CRX 527.

The effect of formulation for the anti-cancer activity observed with CRX-527 was evaluated in the MOT tumor model. In the experiment shown in FIG. 5, C3H/HeN mice (wild-type TLR4, 10 per group) were seeded with MOT tumor ($10^4$ tumor cells IP) on day 0. Mitomycin C (40 ug IP) was administered on day 6, and 1 or 10 ug CRX-527 formulated in AF (Aqueous Formulation=0.02% dipalmitoyl phosphatidyl choline in water), IN (Intranasal Formulation=2% glycerol in water) or SE (Stable Emulsion=2% squalene oil-in-water) was administered via the IP route on day 7. Once again, treatment with mitomycin C alone led to a small increase in survival compared to the no treatment control. Administration of CRX-527 one day after mitomycin C treatment led to prolonged survival, with the SE and IN formulations having enhanced potency compared to the AF formulation. The enhanced potency for the SE and IN formulations is demonstrated in FIGS. 5 and 6, where it can be seen that a 10 ug dose of CRX-527 in the AF formulation was required to induce a high level of protection, while both the SE and IN formulations are highly effective at both the 1 and 10 ug doses. The results of this experiment indicate that the potency of CRX-527 in this model can be enhanced through formulation.

Example 5 Induction of Adaptive Immunity

Figure 7:
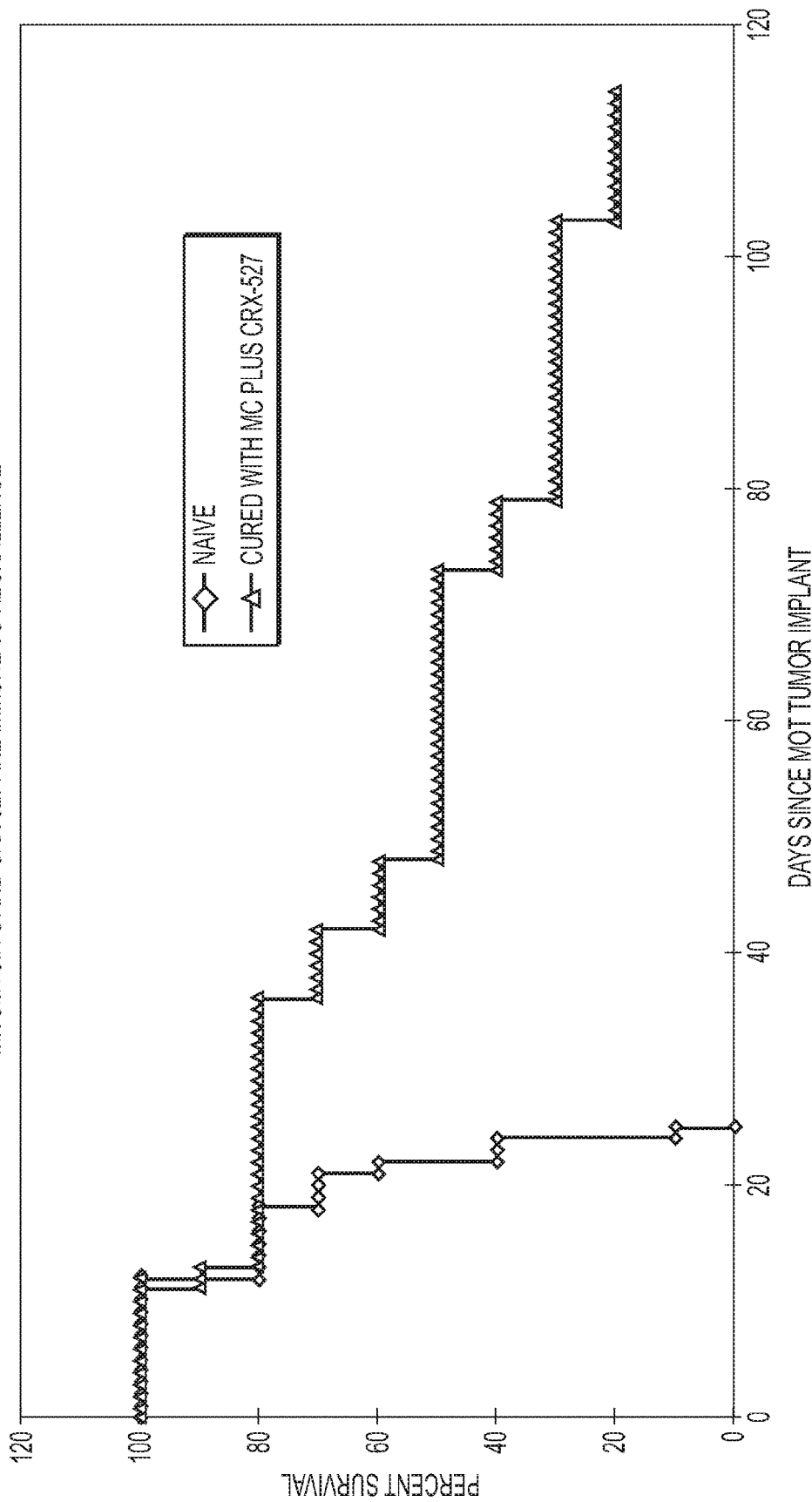
FIG. 7 is a graph showing single combination treatment of Mitomycin-C and CRX-527.

The data shown in FIG. 7 demonstrate that mice cured of MOT tumor by combination treatment with mitomycin C and CRX-527 are resistant to re-challenge with the same tumor (compared to naïve control mice, which succumbed at a normal rate based on historical data). This result indicates that a tumor-specific adaptive immune response is generated in treated/cured mice that is able slow the growth of the tumor and prolong survival upon re-challenge. Group size was 10 in this experiment.

Figure 8:
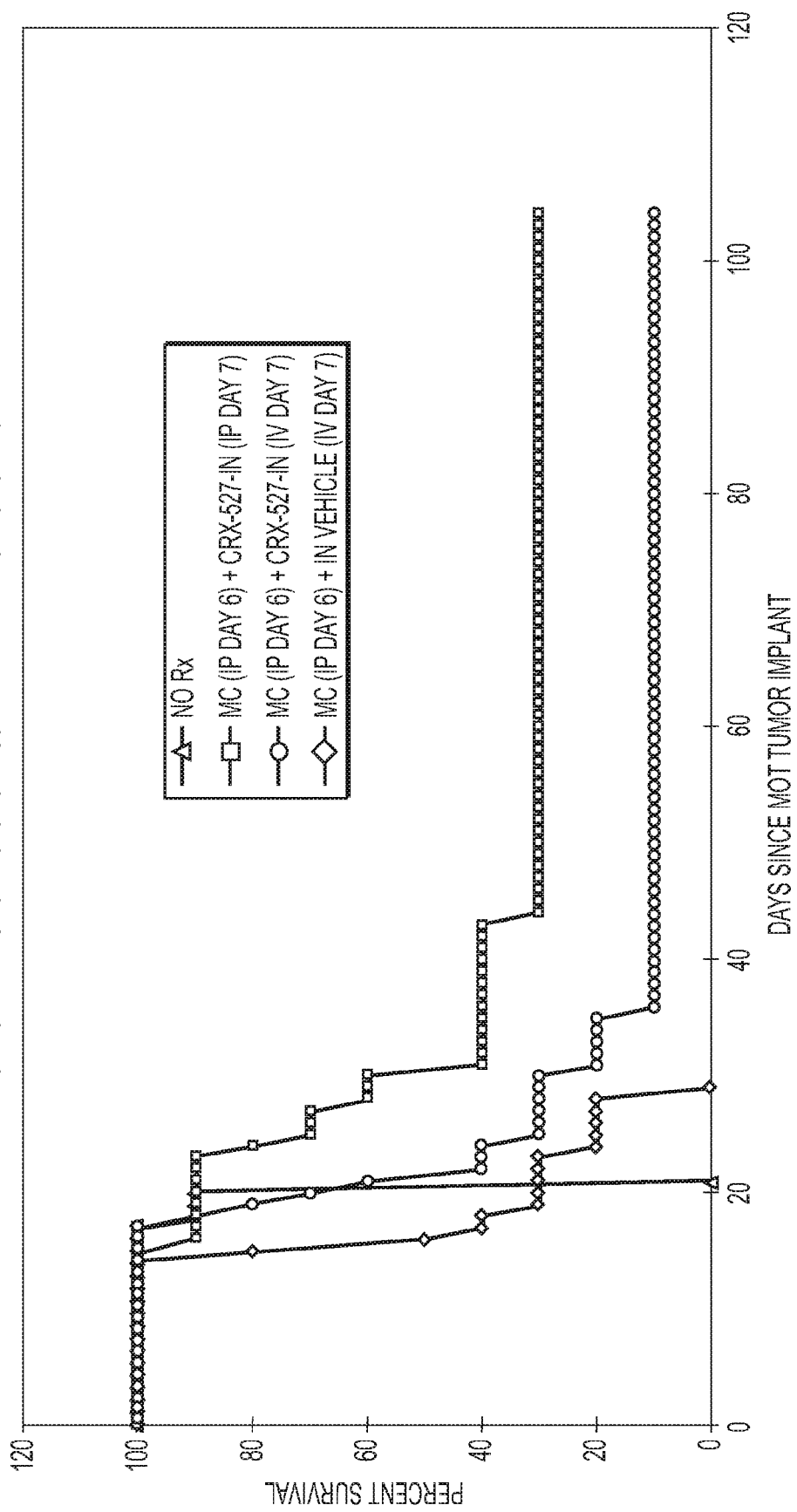
FIG. 8 is a graph showing results of a single regional treatment with Mitomycin-C followed by a systemic treatment with CRX-527.
Figure 9:
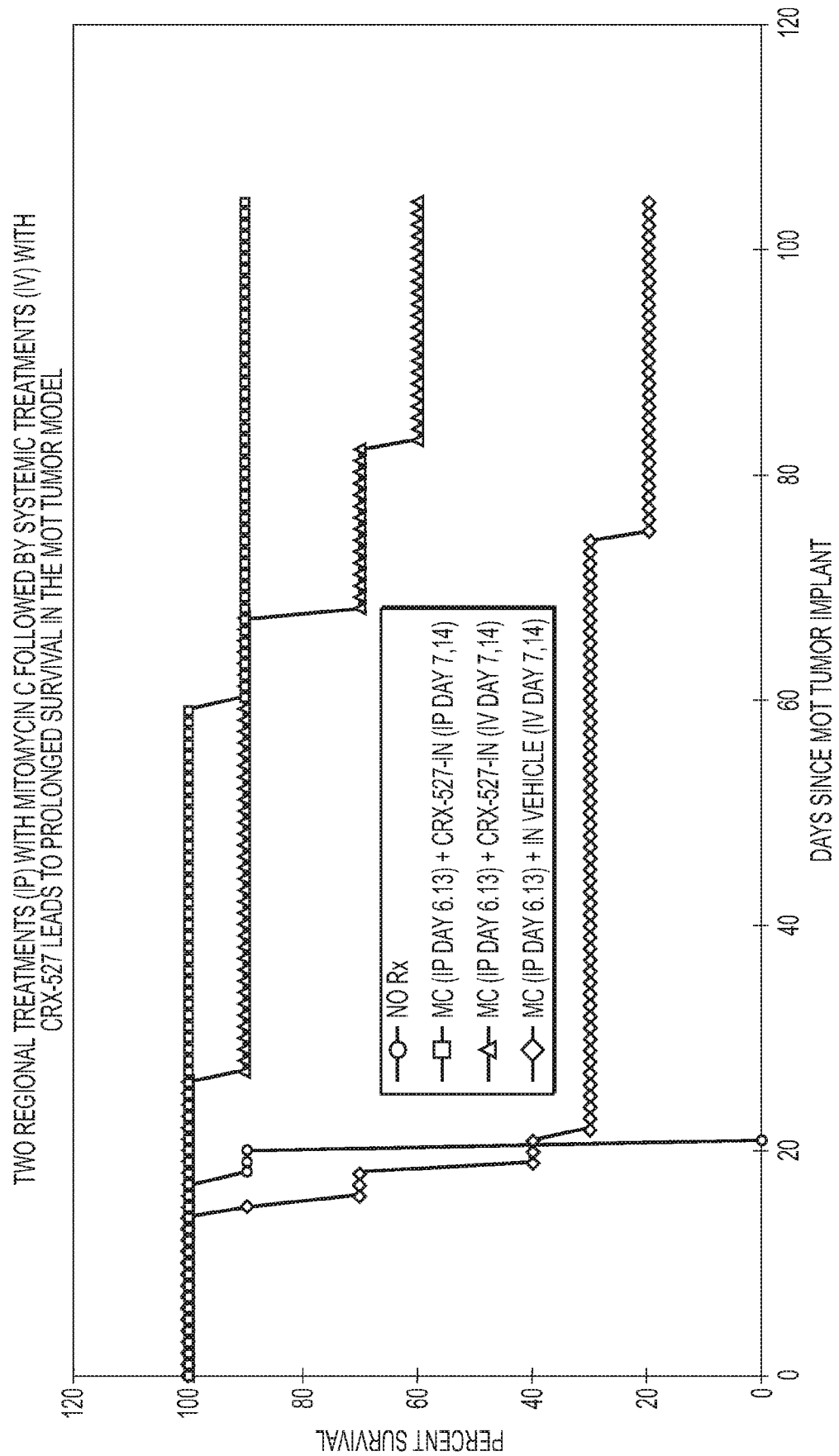
FIG. 9 is a graph showing two regional treatments with Mitomycin-C followed by systemic treatments with CRX 527.

Example 6 Effect of Multiple Treatments And Effect of Regional Versus Systemic Administration of Immunomodulator The data presented in FIGS. 8 and 9 demonstrates that the components of the combination therapy can be successfully administered by different routes. In this experiment, mitomycin C was administered to MOT-bearing mice via the IP route, and the CRX-527-IN was administered by either the IP or IV routes. While the prolongation of survival was more striking in the group that received both components via the IP route, the group that received mitomycin C via the IP route and CRX-527-IN via the IV route was also protected, especially after two administration of the combination therapy. The data presented in FIGS. 8 and 9 also demonstrate that two treatments with the combination therapy is more effective than one treatment for prolonging survival in the MOT tumor model. This result indicates that the number of treatments may have an effect on the outcome for such therapeutics.

Example 7 B16 Melanoma System

Figure 10:
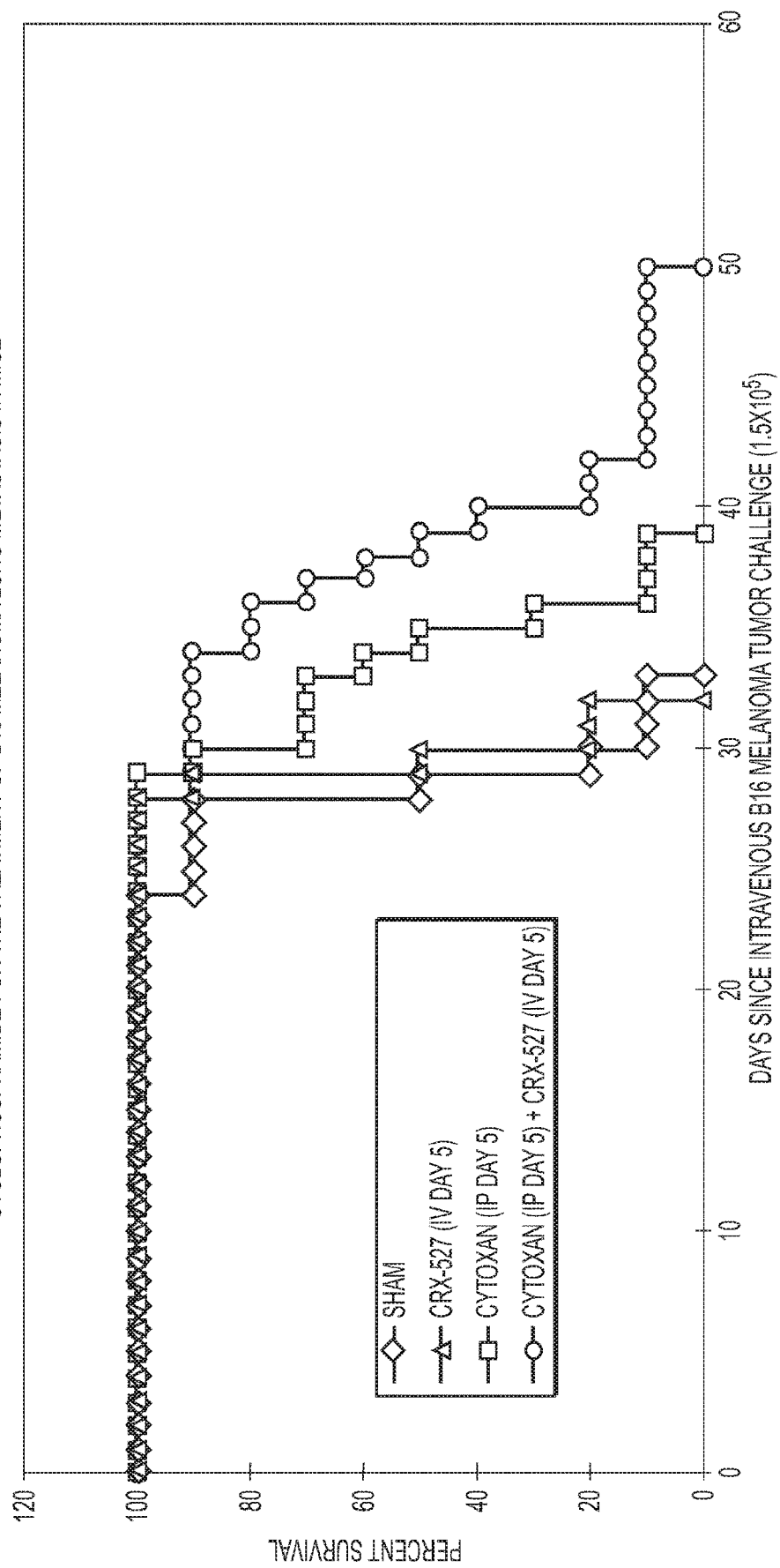
FIG. 10 is a graph showing Intravenous CRX-527 IN combined with IP cyclophosphamide treating B16 melanoma lung metastasis in mice.
Figure 11:
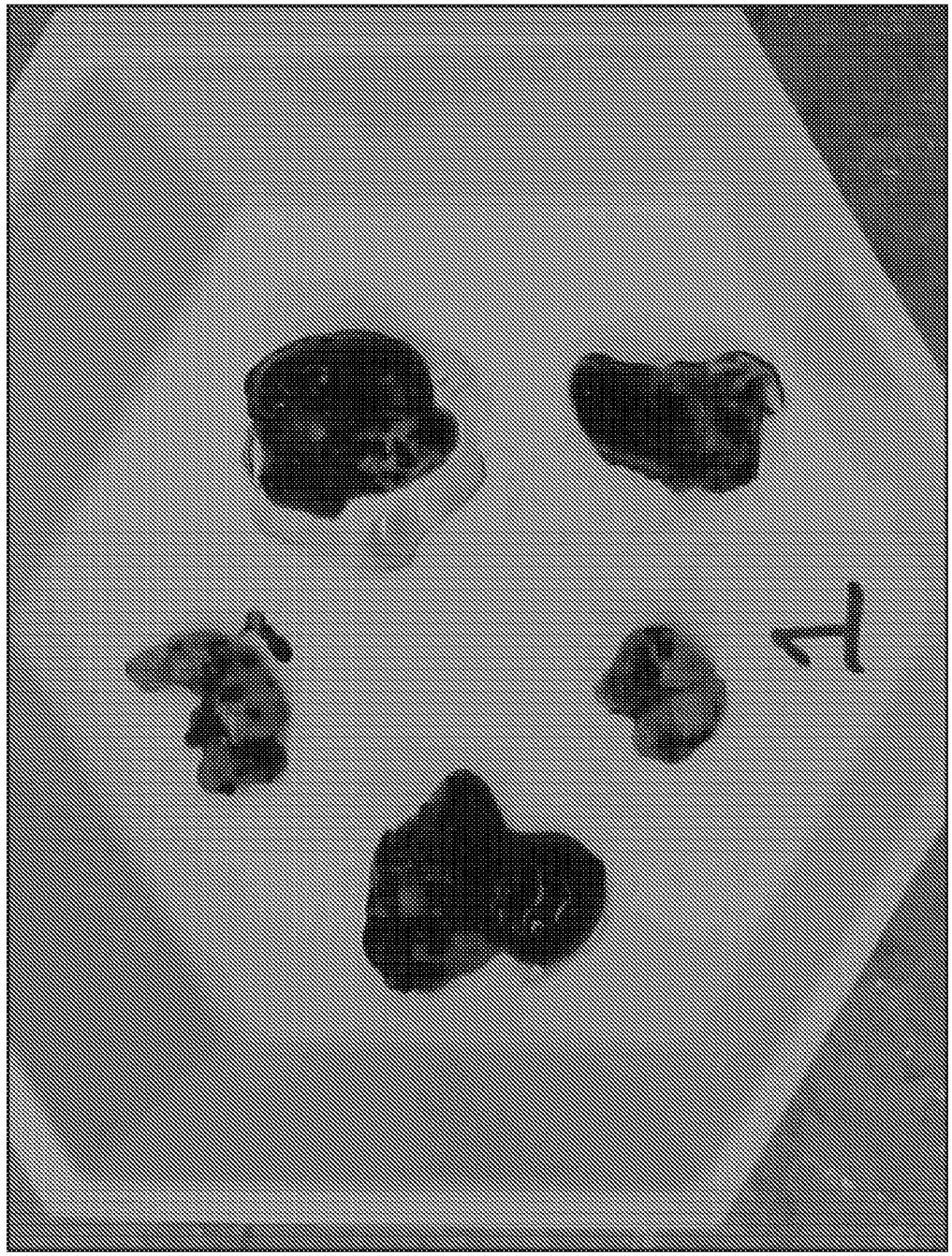
FIG. 11-14 are photographs of tumors in the lungs of mice treated with vehicle, CRX-527 alone, cyclophosphamide alone and CRX-527 with cyclophosphamide.
Figure 12:
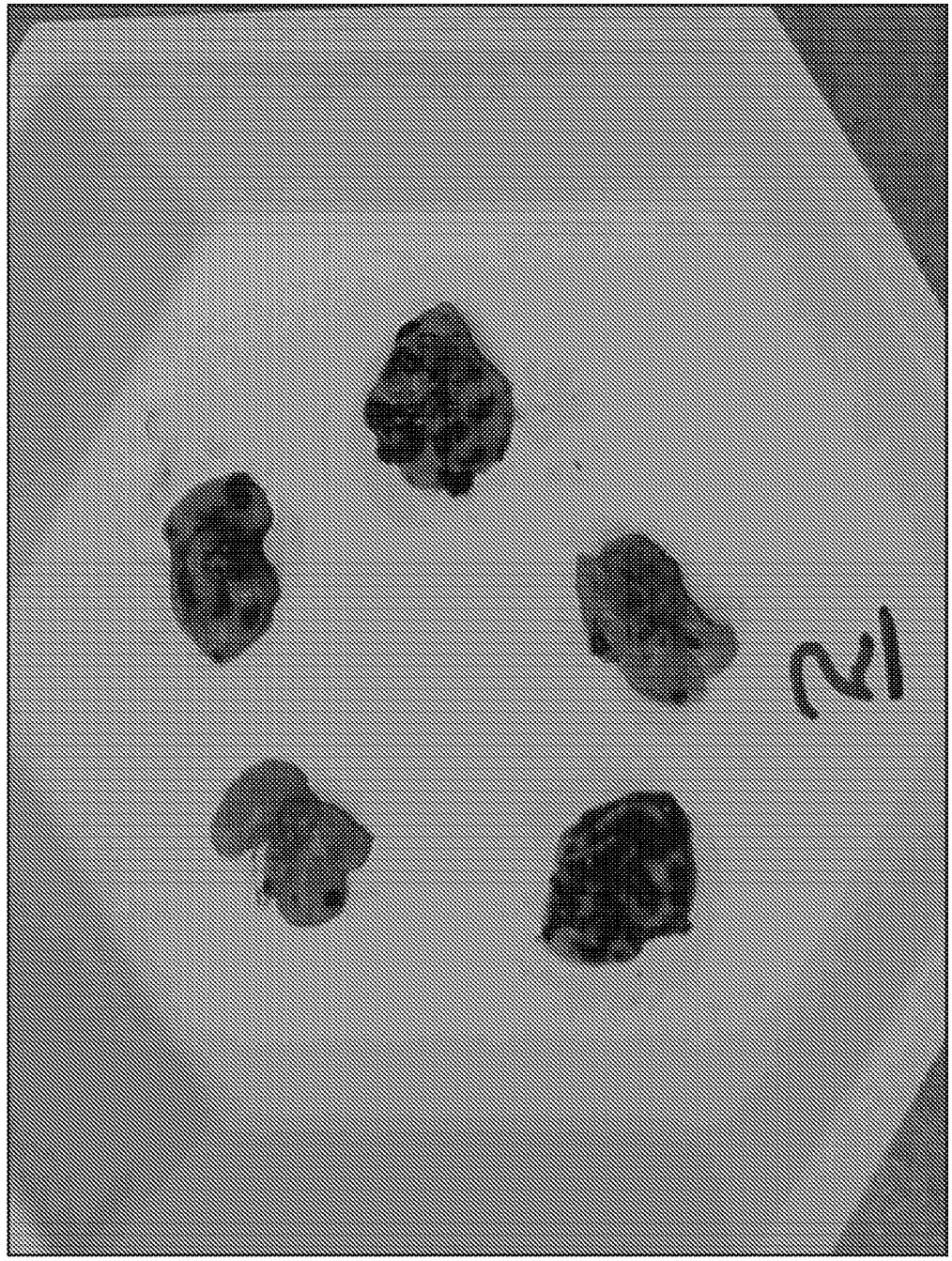
Figure 13:
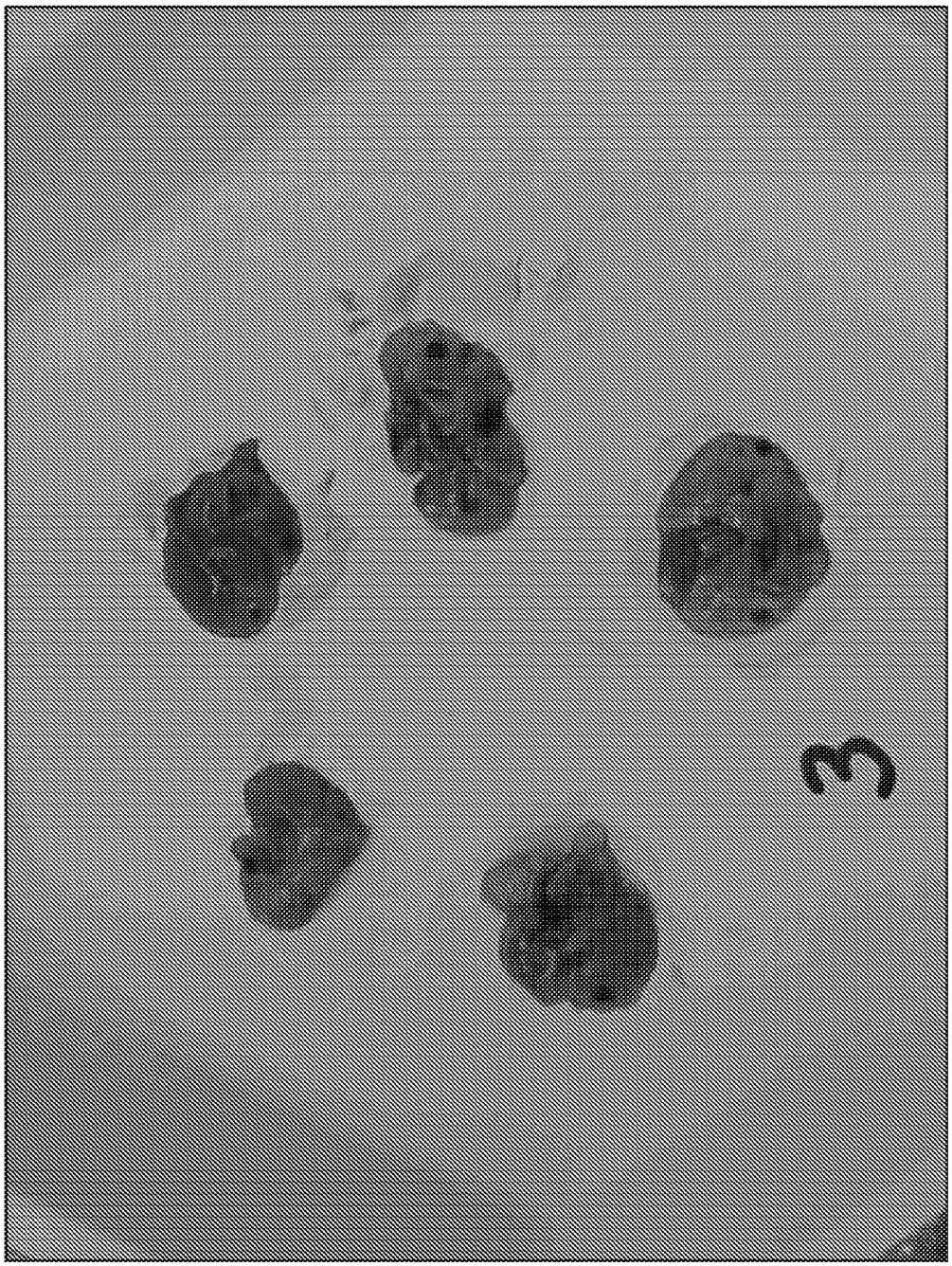

The efficacy of combination therapy with a chemotherapeutic agent and an AGP was also tested in a murine melanoma model using a non-immunogenic tumor called B16-F10. In these experiments, BDF1 mice were seeded with B16-F10 melanoma cells ($1.5 \times 10^3$ IV) on day 0. At various time thereafter, cancer-bearing mice were treated with cyclophosphamide (aka Cytoxan) alone (3 mg IP), CRX-527-IN (10 ug) alone or a combination of the two agents. As shown in FIG. 10, treatment with CRX-527-IN alone on day 5 did not lead to a improve survival, while treatment with cyclophosphamide alone on day 5 led to a modest prolongation. However, the group administered CRX-527-IN and cyclophosphamide together showed an improvement in survival compared to the other groups.

Figure 14:
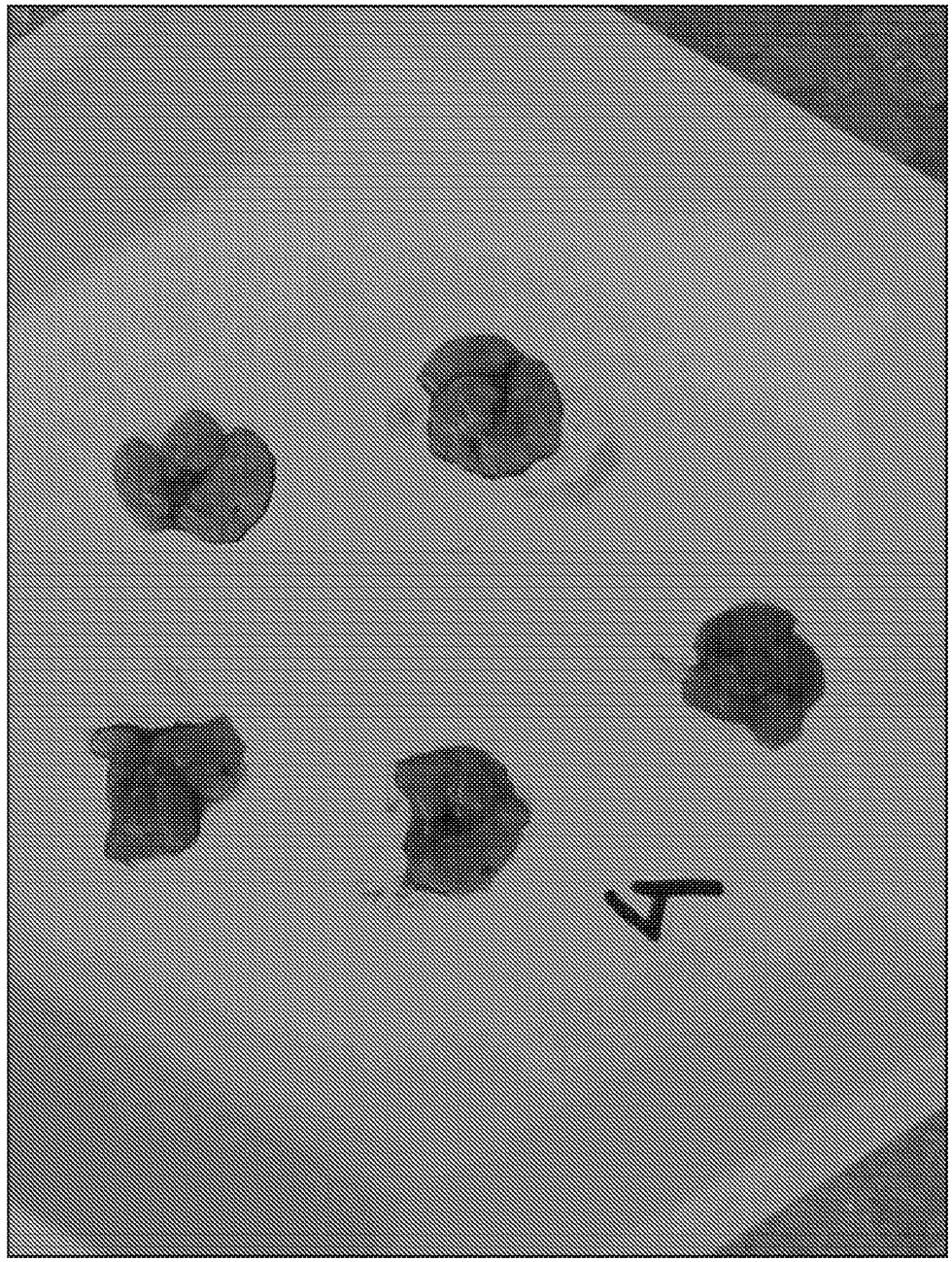
Figure 15:
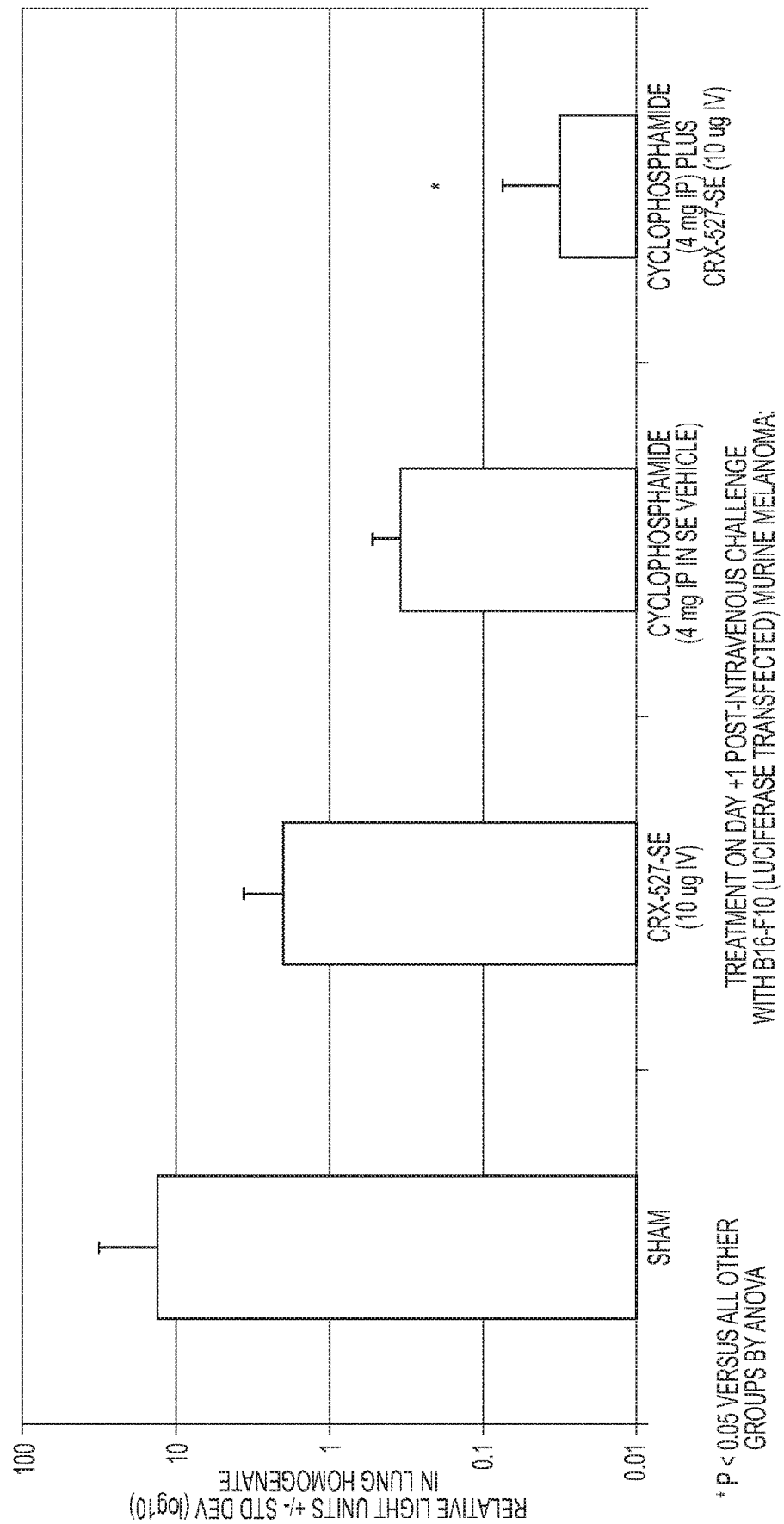
FIG. 15 is a graph showing tumor growth in lungs of mice (as measured by luciferase activity) following treatment with vehicle, CRX-527 alone, cyclophosphamide alone and CRX-527 with cyclophosphamide.

In further experimentation, B16-F10 melanoma cells transfected with green fluorescent protein were used to quantify metastasis of the tumor to the lungs of mice. Because green fluorescent protein allows quantification of the amount of tumor in the lungs of B16-F10-bearing mice, it was possible to evaluate the efficacy of various treatment regimens using lung tumor burden as the read-out. BDF1 mice were seeded with B16-F10 melanoma cells ($1.5 \times 10^3$ IV) on day 0. Tumor-bearing mice (5 per group) were injected on day 1 with vehicles (500 ul saline IP and 100 ul SE vehicle IV), CRX-527-SE (10 ug in 100 ul IV), cyclophosphamide (4 mg in 500 ul water IP) or both CRX-527-SE (10 ug in 100 ul IV) and cyclophosphamide (4 mg in 500 ul water IP). On day 26, the mice were sacrificed and their lungs were collected. The lungs from each mouse were photographed and then homogenized so that the luciferase activity could be quantified to determine how much B16-F10 tumor was present. By visual examination (FIG. 11-14), it is clear that mice treated with the cyclophosphamide/CRX-527 combination (FIG. 14) had lower lung tumor burden than any other group. This observation was confirmed when the lungs were homogenized and evaluated for luciferase activity. The data presented in FIG. 15 show that lungs from mice treated with the cyclophosphamide and CRX-527 had significantly less luciferase activity, and hence less tumor, in their lungs than mice treated with vehicle or either agent alone, confirming the advantage of combination therapy in this sytem.

Example 8 Combination Therapy in Breast Cance Model

Figure 16:
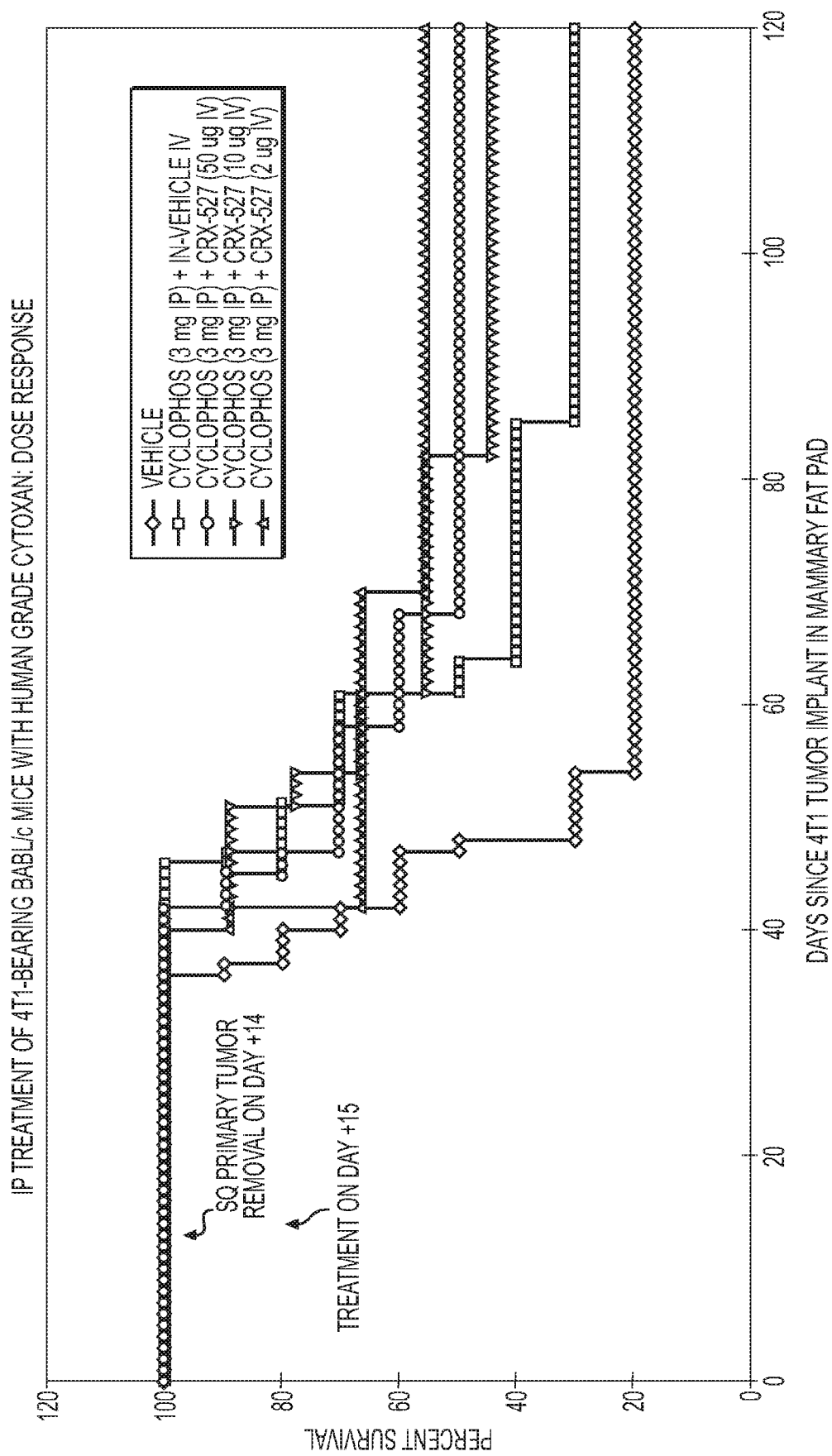
FIG. 16 is a graph showing treatment of 4T1-bearing BALB/c Mice with human grade Cytoxan.

The benefit of combining chemotherapeutic agents with TLR4 ligands such as AGPs was also confirmed in the 4T1 murine breast cancer model. For the experiments conducted using this metastatic cancer model, 4T1 tumor cells ($7 \times 10^3$ in 50 uL) were injected into the lower mammary gland of each mouse on day 0. The primary tumors were surgically removed on day 14, the mice (10 per group) were treated on day 15 with vehicles, cyclophosphamide (3 mg IP) or cyclophosphamide (3 mg IP) and CRX-527 (various doses IV). The results shown in FIG. 16 demonstrate that groups receiving the combination therapy had longer survival times than groups receiving vehicle or cyclophosphamide alone. While not as definitive as the data collected in the L1210, MOT or B16-F10 systems, these results lend support to claims that combination therapy with chemotherapeutics and immunomodulators such as CRX-527 is superior to treatment with either alone.

Example 9 Results of CT-26 Study with Treatment with TLR-4 (CRX-527)

The CT26 mouse colon carcinoma (CT26.WT; ATCC #CRL-2638) cell line was obtained from ATCC. It is an N-nitroso-N-methylurethane-(NNMU) induced, undifferentiated colon carcinoma cell line known in the art. For example, it is described in: Wang M, et al. Active immunotherapy of cancer with a nonreplicating recombinant fowlpox virus encoding a model tumor-associated antigen. J. Immunol. 154: 4685-4692, 1995 (PubMed: 7722321), which is incorporated by reference in its entirety herein. For preparation of tumor cells, A frozen (−140° C.) vial of CT-26

(mouse colon carcinoma cells), from ATCC (cat # CRL-2638, lot #59227052) are thawed and cultured in basic RPMI (with 10% FBS) media over the following week.

CT-26 cells (passage 12) are harvested from the flask in complete medium. Cells are centrifuged and resuspended in RPMI (without FBS), this step is repeated 3 times. Cell density and viability are checked via trypan blue exclusion. Cells are then diluted to desired density ($5 \times 10^5$ cells per mL) and kept on ice.

Escalating doses of CRX 527 are evaluated for their efficacy in reducing tumor growth. Animals are weighed and innoculated on the right hind quarter with $0.5 \times 10^5$ CT26 tumor cells per mouse on Day 0. A total of 130 mice are inoculated with tumor cells—assuming 30% failure rate (either too big or too small at time of start of study), the goal is to have n=10 for each group. After tumor cell innoculation, tumor growth and total body weight are measured 3 times a week for the duration of the study. Randomization occurs on day 10 or 11 when the average tumor volume is approximately 100 mm³. Begining on the day of randomization, animals are dosed with CRX 527 or vehicle i.p. biweekly, for a total of 6 doses. Mice remain on study until tumors reach >2000 cu mm for two consecutive measurements, they are removed from study for other reasons (i.e. weight loss >20%, ulceration on tumor, etc.) or until the end of the study. After euthanization the tumors may be removed and subject to dissociation for flow analysis and/or FFPE for IHC analysis.

| | Treatment | Dose (per mouse) | No. of mice |
|---|---|---|---|
| Group 0: | $0.5 \times 10^5$ cells per, | vehicle | 10-13 |
| Group a: | $0.5 \times 10^5$ cells per, | CRX-527; 4 ug | 10-13 |
| Group b: | $0.5 \times 10^5$ cells per, | CRX-527; 20 ug | 10-13 |
| Group c: | $0.5 \times 10^5$ cells per, | CRX-527; 100 ug | 10-13 |

Day 0: sc inoculation with tumor cells
Days 1, 4, 6, 8: Animals were weighed and checked for tumors and measured.
Randomization day (approx. day 10): Animals randomized and placed into cages representing appropriate groups
Dosing, biweekly through end of study: Animals dosed ip with TLR compound CRX-527 at amounts shown above (per mouse), or vehicle.
Measurements, triweekly through end of study: Animals weighed and tumors measured.

Figure 17:
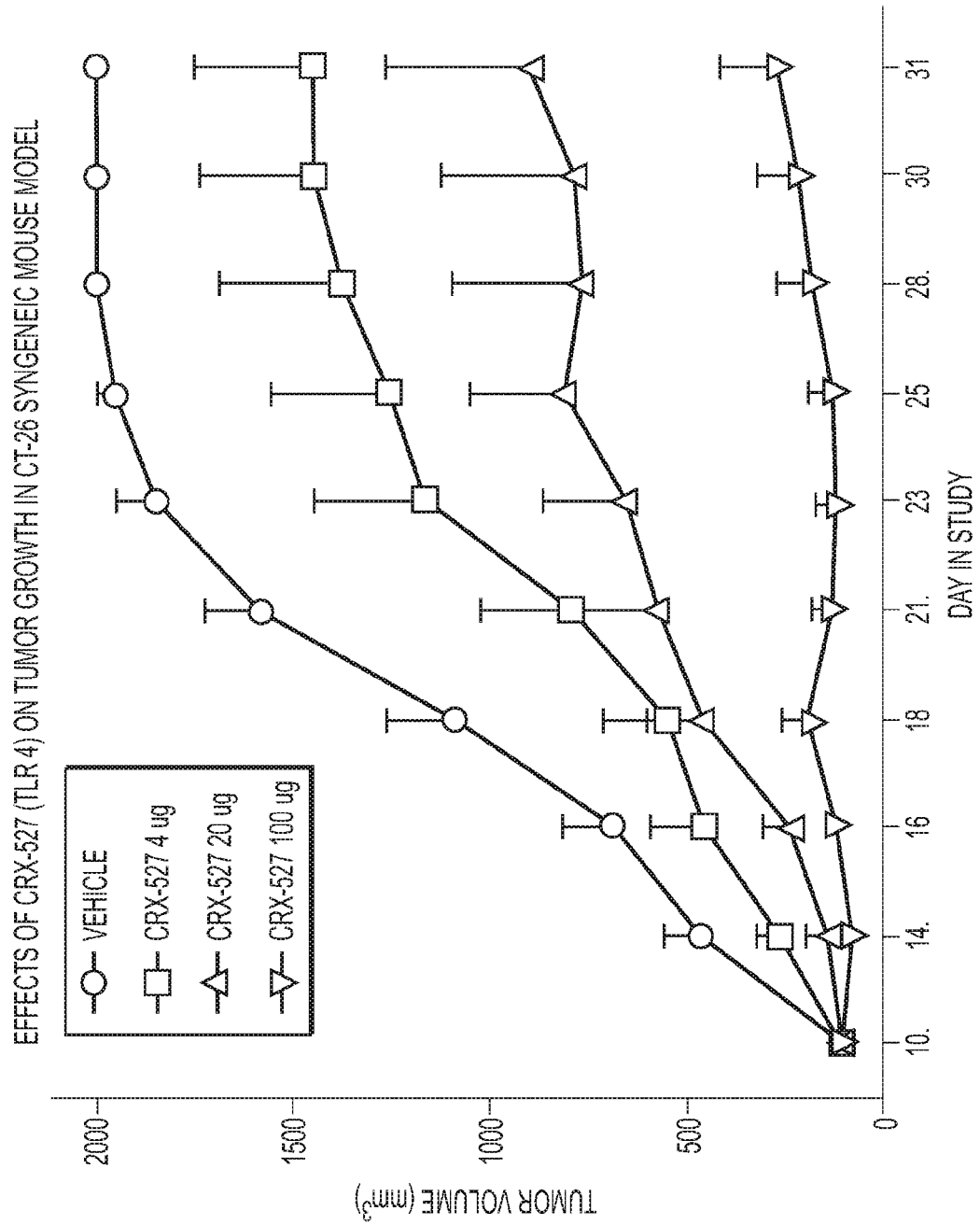
FIG. 17 is a graph showing the effects of CRX-527 (TLR 4) on tumor growth in CT-26 syngeneic mouse model.
Figure 18:
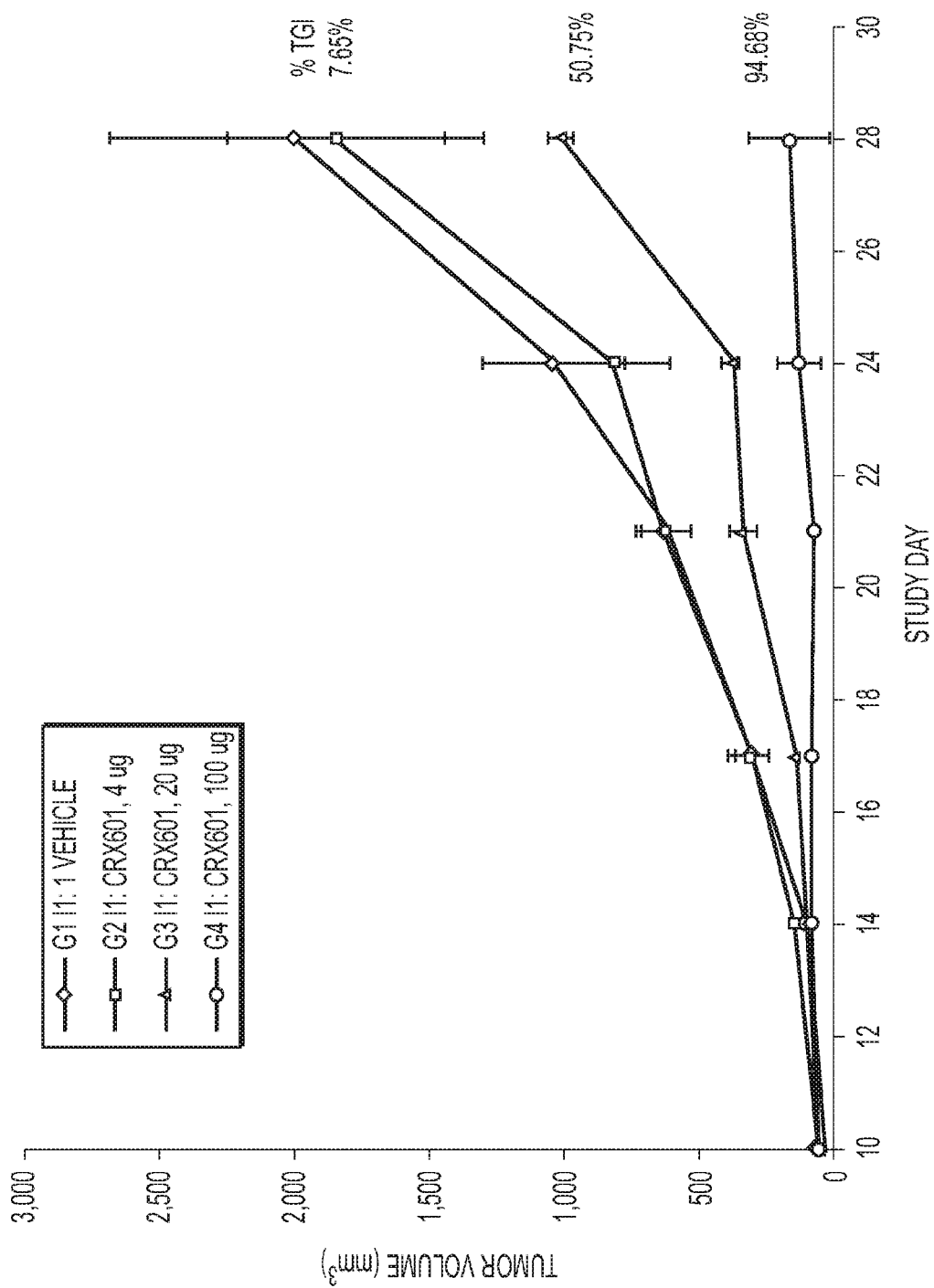
FIG. 18 is a graph showing dose dependent anti-tumor activity (as measured by tumor volume over time) of 4, 20, or 100 ug of TLR-4 agonist (CRX-601) in a CT-26 syngeneic mouse model of colon cancer.

The above protocol was used to generate the results in FIG. 17 at the dosages indicated. In almost every case, Balb/c mice that were inoculated with $0.5 \times 10^5$ CT-26 colorectal tumor cells on the right hind quarter developed tumors that, when treated i.p. with vehicle (2% glycerol) only, and progressed as expected. TLR 4 agonist CRX-527 inhibited tumor growth in a dose dependent manner when compared to the vehicle treated animals. FIG. 17. Dose dependence was also seen in the survivability of the model. In a similar experiment, TLR4 agonist CRX-601 inhibited tumor growth. See Table 2 and FIG. 18.

TABLE 2

| | Mean % Inhibition Date/Study Day | | | | | |
|---|---|---|---|---|---|---|
| | Dosing 9/16 | 9/19 | 9/23 | 9/26 | 9/30 | 10/3 |
| | | | Group | | | |
| Vehicle | 14 | 17 | 21 | 24 | 28 | 31 |
| CRX-601 4 ug | −59.63% | 4.57% | −1.55% | 21.73% | 7.65% | −34.14% |
| CRX-601 20 ug | 42.34% | 69.46% | 50.75% | 66.96% | 50.75% | −18.27% |

TABLE 2-continued

| | Mean % Inhibition Date/Study Day | | | | | |
|---|---|---|---|---|---|---|
| | Dosing 9/16 | 9/19 | 9/23 | 9/26 | 9/30 | 10/3 |
| | | | Group | | | |
| Vehicle | 14 | 17 | 21 | 24 | 28 | 31 |
| CRX-601 100 ug | 68.20% | 92.51% | 98.50% | 93.21% | 94.68% | 80.15% |

Example 10 Monotherapy and Combination Treatment with Anti-Cancer Agent and TLR-4 Targeting Molecules of Formula I Materials and Methods In vivo anti-tumor efficacy studies The in vivo anti-tumor efficacy of the TLR4 agonist (CRX-601) was assessed in the murine CT-26 colon carcinoma syngeneic solid tumor model as a monotherapy and in combination with a rate a therapeutic antibody (combination data not shown). Seven to eight week old female Balb/c mice (BALB/cAnNCrl, Charles River) were used in these studies. Murine CT-26 colon carcinoma cells (ATCC catalog number CRL-2638 lot #59227052) were cultured in RPMI growth medium supplemented with 10% fetal bovine serum (FBS) in a humidified 37° C. incubator with 5% $CO_2$, CT-26 cells cultured in logarithmic growth were harvested from tissue culture flasks and centrifuged for 5 minutes at 450×g at 4° C. for ten minutes to pellet cells. The supernatant was discarded, and cells were washed in ice cold phosphate buffered saline (PBS) without calcium and magnesium and centrifuged again for 5 minutes at 450×g at 4° C. for ten minutes to pellet cells. The cells were resuspended in sterile RPMI media without FBS and adjusted to a cell concentration of 500,000 cells/ml, 100 μl of the cell stock was implanted via subcutaneous injection into the right flank of each Balb/c mouse. After ten or eleven days when the average tumor size reached approximately 100 mm³, mice were randomized into study cohorts according to tumor size and the first treatment dose was given. The TLR4 agonist (CRX-601) or vehicle was dosed via a systemic intravenous or direct intratumoral injection as indicated. The CRX-601 vehicle used for intravenous and intratumoral dosing was 0.5% where indicated. For CRX-601 liposomal intratumoral dosing, a DOPC/CHOL liposome prepared by GSK Lot #1783-157-B was used. The therapeutic antibody was dosed via an intraperitoneal injection given twice per week for a total of six doses. Caliper measurements were taken three times per week to assess tumor growth, and mice with tumors <2,000 mm³ were maintained on study from 30 up to approximately 115 days. Mice with tumors >2,000 mm³ for 2 consecutive measurements or mice with tumors which formed open ulcers were removed from the study. Tumor volume was calculated using the formula (0.52)×(Length)×(Width²). In study 3, tumor-free mice were re-challenged with CT-26 tumor cells as described above, on the opposite flank from the original inoculation site and tumor growth was monitored, as described above. All studies were conducted in accordance with the GSK Policy on the Care, Welfare and Treatment of Laboratory Animals and were reviewed by the Institutional Animal Care and Use Committee at GSK.

Immunephenotyping and Cytokine Analysis

Tumors, blood and tissues were harvested from CT-26 mice on day 0, day 1 and day 8 after first CRX-601 dosing. Mouse white blood cells and dissociated tumor single cells were stained freshly with surface or intracellular staining antibodies for multicolor flow cytometry analysis for immunephenotyping. Multiplex cytokine analysis was performed using mouse plasma samples from the same study.

Statistical Analysis

For studies 1 and 2, to determine significance of tumor growth inhibition, tumor volumes at 11 study 1) or 15 (study 2) days after first dose were compared between the different treatment groups. Prior to the analysis, tumor volumes were natural log transformed due to the inequality of variance in the different treatment groups. ANOVA followed by pair-wise comparison was then carried out on the log transformed data. SAS 9.3 and R 3.0.2 analysis software was used. Kaplan-Meier (KM) method was carried out to estimate the survival probability of different treatment groups at a given time. The event for survival analysis was tumor volume of 2000 mm$^3$ or tumor ulceration, whichever came first. The exact time to cut-off volume was estimated by fitting a linear line between log tumor volume and day of two observations, the first observation that exceed the cut-off volume and the one observation that immediately preceded the cut-off volume. The median time to endpoint and its corresponding 95% confidence interval was calculated. Whether or not KM survival curves were statistically different between any two groups was then tested by log-rank test. The raw p-value, as well as the false discovery rate (FDR) adjusted p-values, from the comparisons of days to events by survival analysis and the comparisons of log transformed tumor volume at indicated days between treatment groups was determined. The ones with FDR adjusted p-values≤0.05 were declared to be statistically significant.

For study 3, to determine the significance of tumor growth inhibition, tumor volumes at 12 days after first dose were compared between the different treatment groups. Treatments were compared by standard ANOVA methods followed by FDR adjustment for multiplicity. Response is square root of volume, for homoscedasticity (equal variance) reasons. Kaplan-Meier (KM) method was carried out to estimate the survival probability of different treatment groups at a given time. For these survival analyses, "Death" means crossing the tumor volume cutoff (2000 mm3). "Survival" means proportion of mice not "Dead", and "Survival time" means days until "Death". If a mouse crossed the volume cutoff between two measurement days, then the day of "death" was estimated by linear interpolation. If a mouse crossed the volume cutoff more than once, the first crossing was used. Treatments were compared by the standard log-rank test for two treatments. The log-rank p-values were adjusted for multiplicity using the FDR (false discovery rate) method. Significance was defined as FDR<=0.05. All calculations and graphs were done using R software, version 3.2.3.

Results

The studies 1-3 were conducted to assess tumor size and survival time in mice treated with CRX-601 and a therapeutic antibody, both alone and in combination with each other.

Study 1

In order to determine CRX-601 monotherapy activity with intratumoral dosing, mice were inoculated with 5×10$^4$ CT-26 cells and randomized into groups of 10 listed below when tumor size reached approximately 100 mm$^3$ as described in Materials and Methods.

Group 1: Vehicle dosed intratumoral twice per week for 6 doses total

Figure 19:
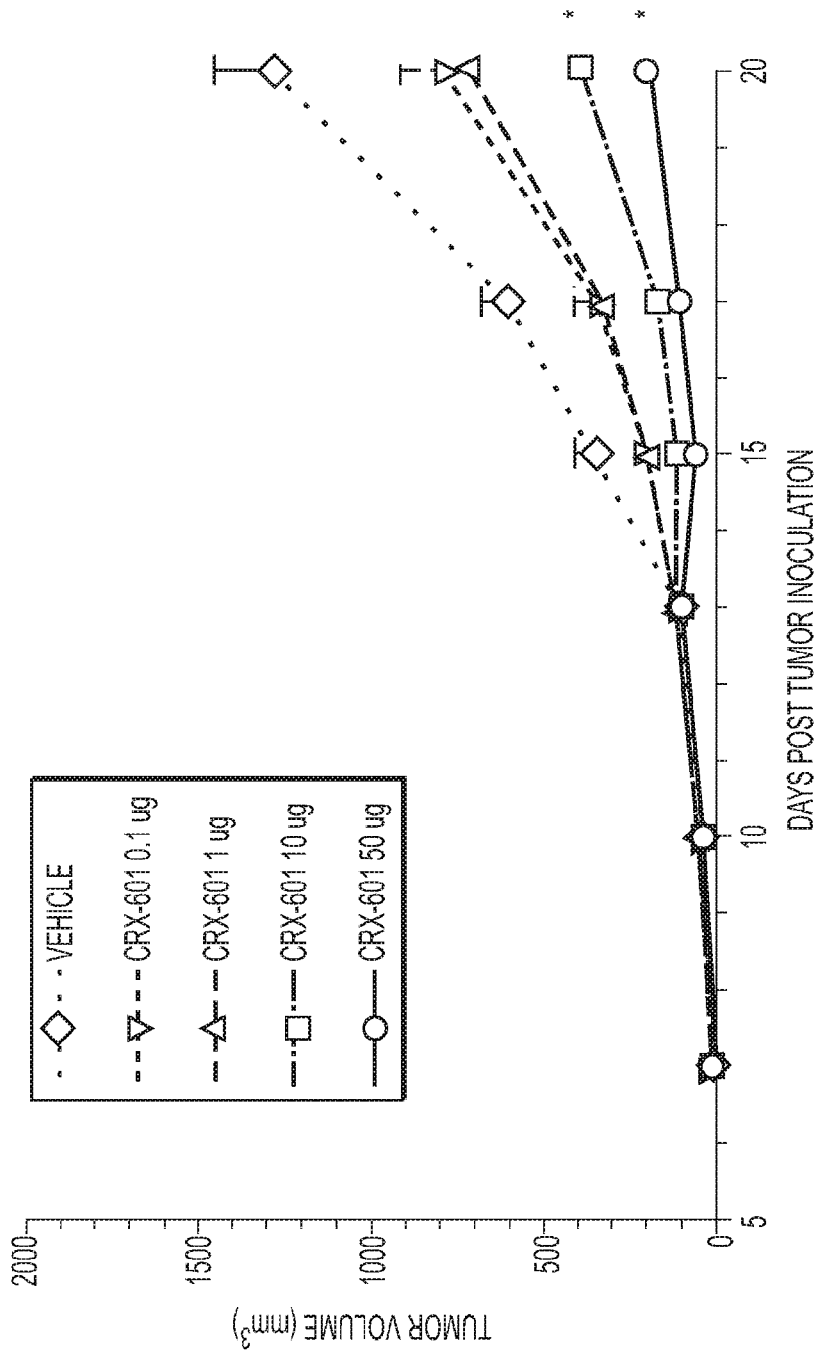
FIG. 19 is a graph showing dose dependent anti-tumor activity of CRX-601 administered intratumorally CT26 Syngeneic mouse model.

Group 2: CRX-601 0.1 ug/mouse dosed intratumoral twice per week for 6 doses total Group 3: CRX-601 1 ug/mouse dosed intratumoral twice per week for 6 doses total Group 4: CRX-601 10 ug/mouse dosed intratumoral twice per week for 6 doses total Group 5: CRX-601 50 ug/mouse single dose With intratumoral dosing, dose-dependent anti-tumor activity (as measured by tumor growth inhibition over time) was observed for the TLR4 agonist CRX-601 in the CT-26 syngeneic mouse tumor model. The 10 μg and 50 μg dosed mice showed statistically significant (*p-values 0.05) tumor growth inhibition 11 days after the initial dose compared to vehicle. Results are shown in FIG. 19.

Figure 20:
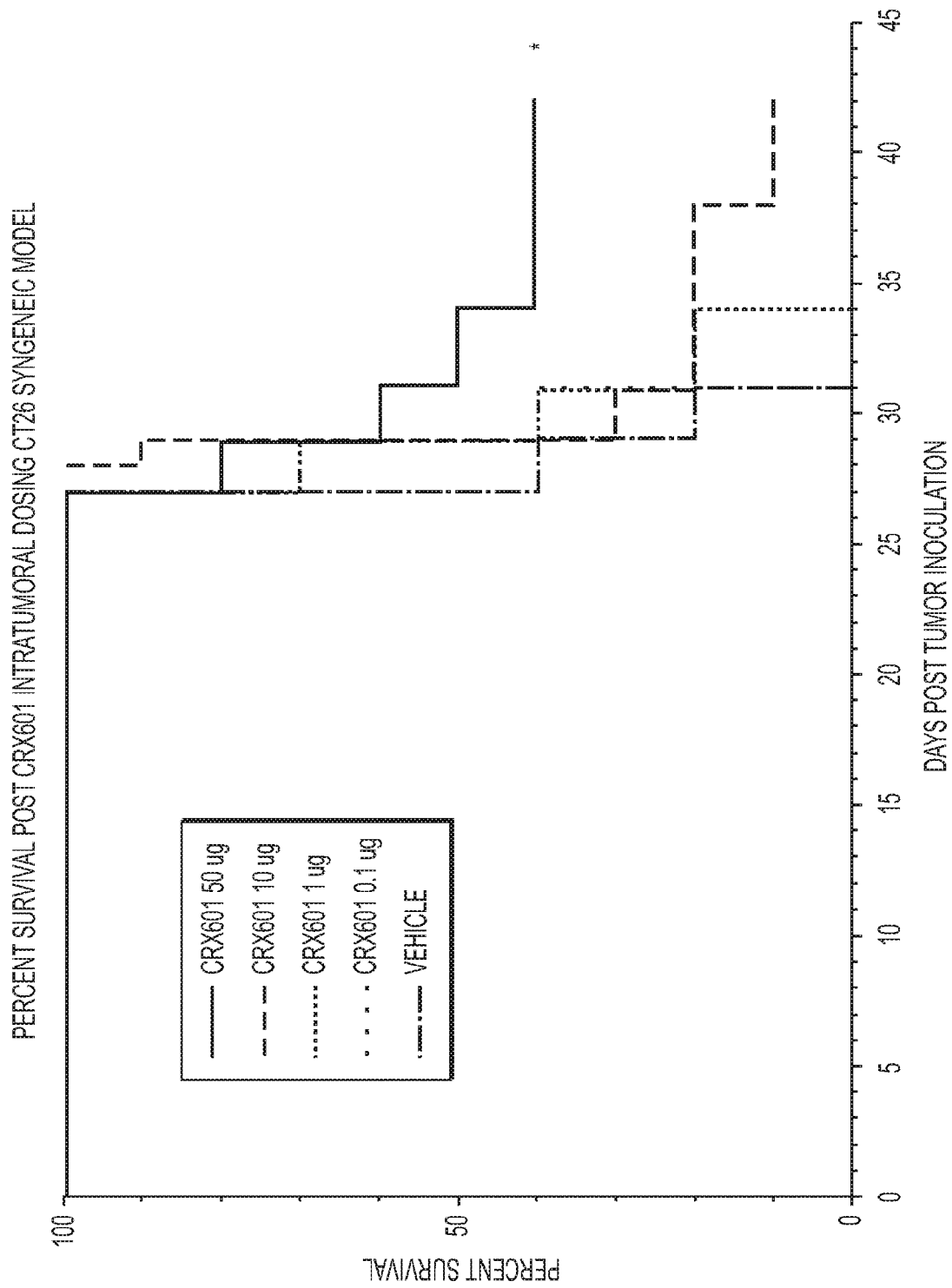
FIG. 20 is a graph showing dose dependent survival benefits of CRX-601 administered intratumorally in a CT26 Syngeneic mouse model.

Mice treated with the TLR4 agonist CRX-601 in this study also showed a statistically significant increase in survival time. The 50 μg dosed mice showed a statistically significant (*p-values≤0.05) increase in survival compared to vehicle by day 42 post CT26 tumor cell inoculation when the study was ended. On this day, only mice from the 50 ug and 10 ug CRX-601 groups remained on study. Three of the four mice in the 50 μg group were tumor-free, with the fourth mouse showing a tumor volume of 854.19 mm$^3$. The single mouse remaining in the 10 μg group was tumor-free. (see FIG. 20).

Study 2

In order to determine CRX-601 monotherapy activity with intravenous dosing, mice were inoculated with 5×10$^4$ CT-26 cells and randomized into groups of 10 below when tumor size reached approximately 100 mm$^3$ as described in Materials and Methods.

Group 1: Vehicle dosed intravenous twice per week for 6 doses total

Group 2: CRX-601 1 ug/mouse dosed intravenous twice per week for 6 doses total

Group 3: CRX-601 10 ug/mouse dosed intravenous twice per week for 6 doses total

Group 4: CRX-601 100 ug/mouse single dose

Figure 21:
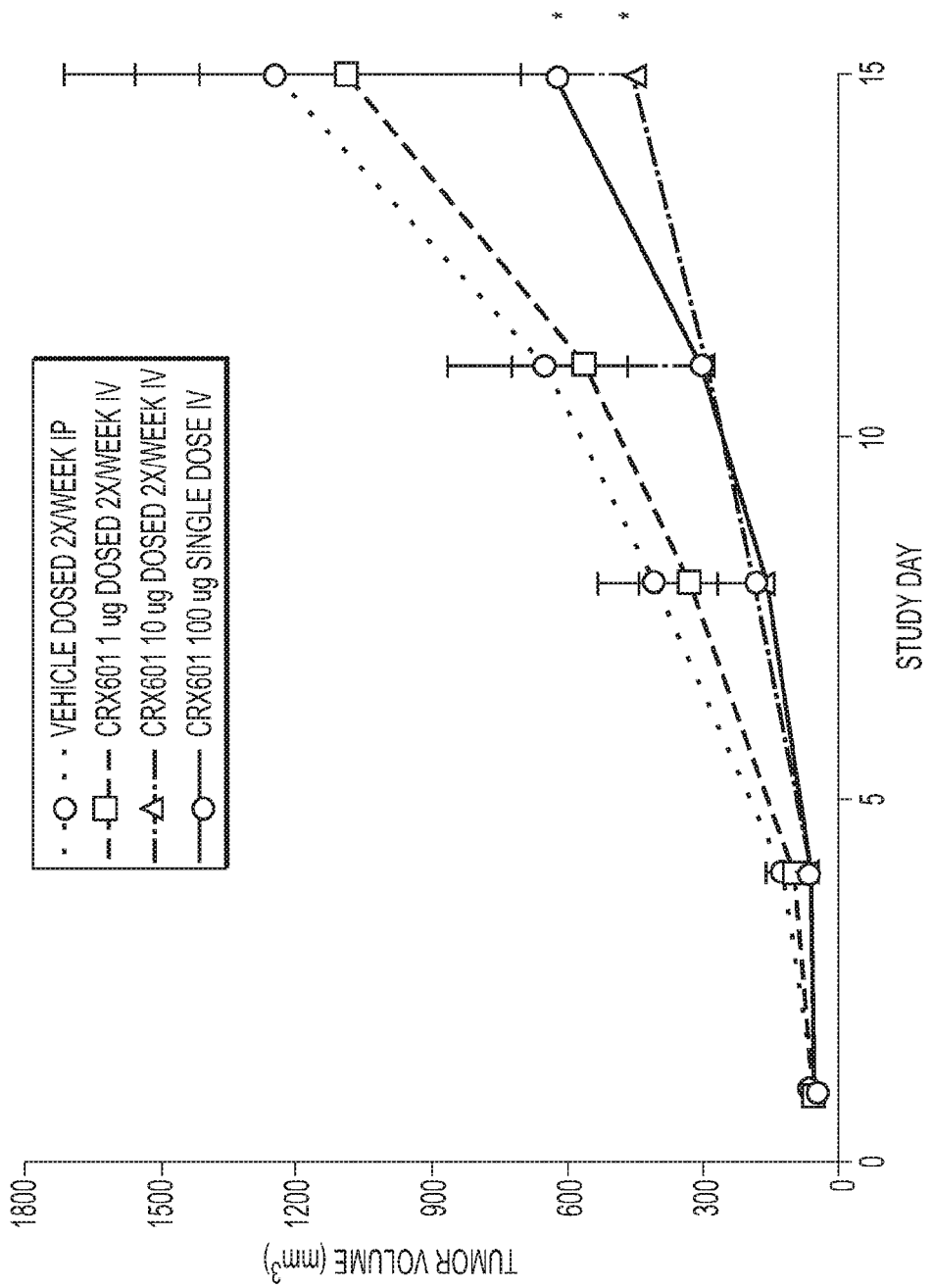
FIG. 21 is a graph showing dose dependent anti-tumor activity of CRX-601 administered intravenously in a CT26 Syngeneic mouse model.

With intravenous dosing, dose-dependent anti-tumor activity (as measured by tumor growth inhibition over time) was observed for the TLR4 agonist CRX-601 in this CT-26 syngeneic mouse tumor model. The 10 μg and 100 μg dosed mice showed statistically significant (*p-values≤0.05) tumor growth inhibition 15 days after the initial dose compared to vehicle (see FIG. 21).

Figure 22:
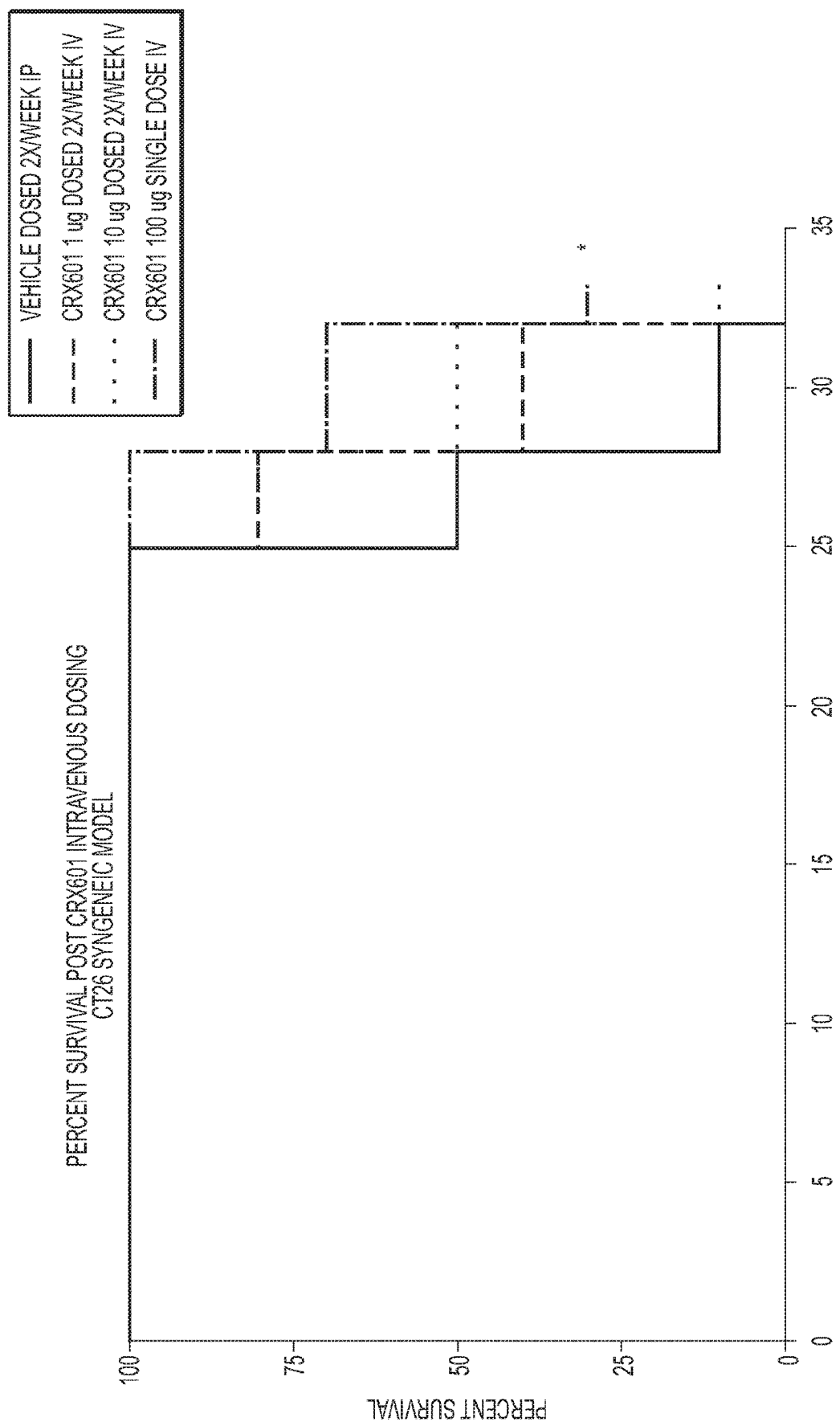
FIG. 22 is a graph showing survival benefits of CRX-601 administered intravenously in a CT26 Syngeneic mouse model

Mice treated with the TLR4 agonist CRX-601 in this CT-26 syngeneic mouse tumor model also showed statistically significant increase in survival compared with vehicle. The 100 μg dosed mice showed a statistically significant increase (*p-values≤0.05) in survival compared to vehicle when the study was ended on day 32 post CT-26 tumor cell inoculation. One of the three mice remaining in this group was tumor-free, while the other mice showed tumor volumes of 1500.49 and 962.61 mm$^3$. The single mouse remaining in the 10 μg dose group had a tumor volume of 188.0 mm$^3$. (See FIG. 22)

Study 3

As part of combination studies comparing CRX-601 activity alone and in combination with a therapeutic antibody (combination data not shown) CRX-601 was dosed either intravenous (IV) using a 0.5% Glycerol/4% dextrose vehicle, or intratumoral (IT) using a DOPC/CHOL liposomal formulation, and mice were inoculated with 5×10$^4$CT-26 cells and randomized into groups of 10 below when tumor size reached approximately 100 mm$^3$ as described in Materials and Methods. Groups 1 and 5 were control groups for the intravenous/intraperontonel and intratumoral/intraperontonel, respectively. Groups 2 and 7 were administered CRX-601. Groups 3, 4, 6, and 8 were administered a combination of CRX-601 and a therapeutic antibody (combination data not shown).

Figure 23:
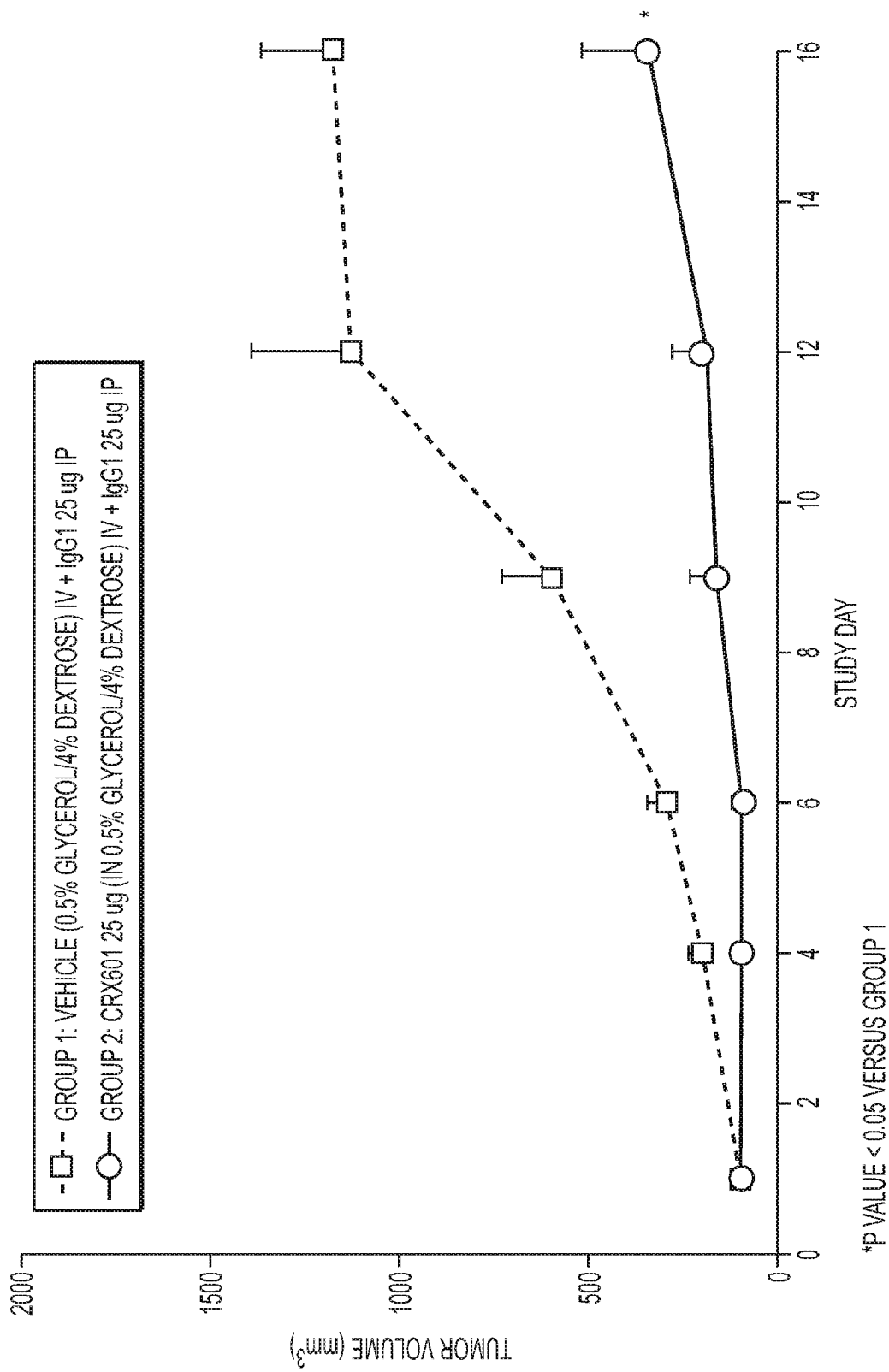
FIG. 23 is a graph showing anti-tumor activity of CRX-601 administered intravenously in a CT26 Syngeneic mouse model.
Figure 24:
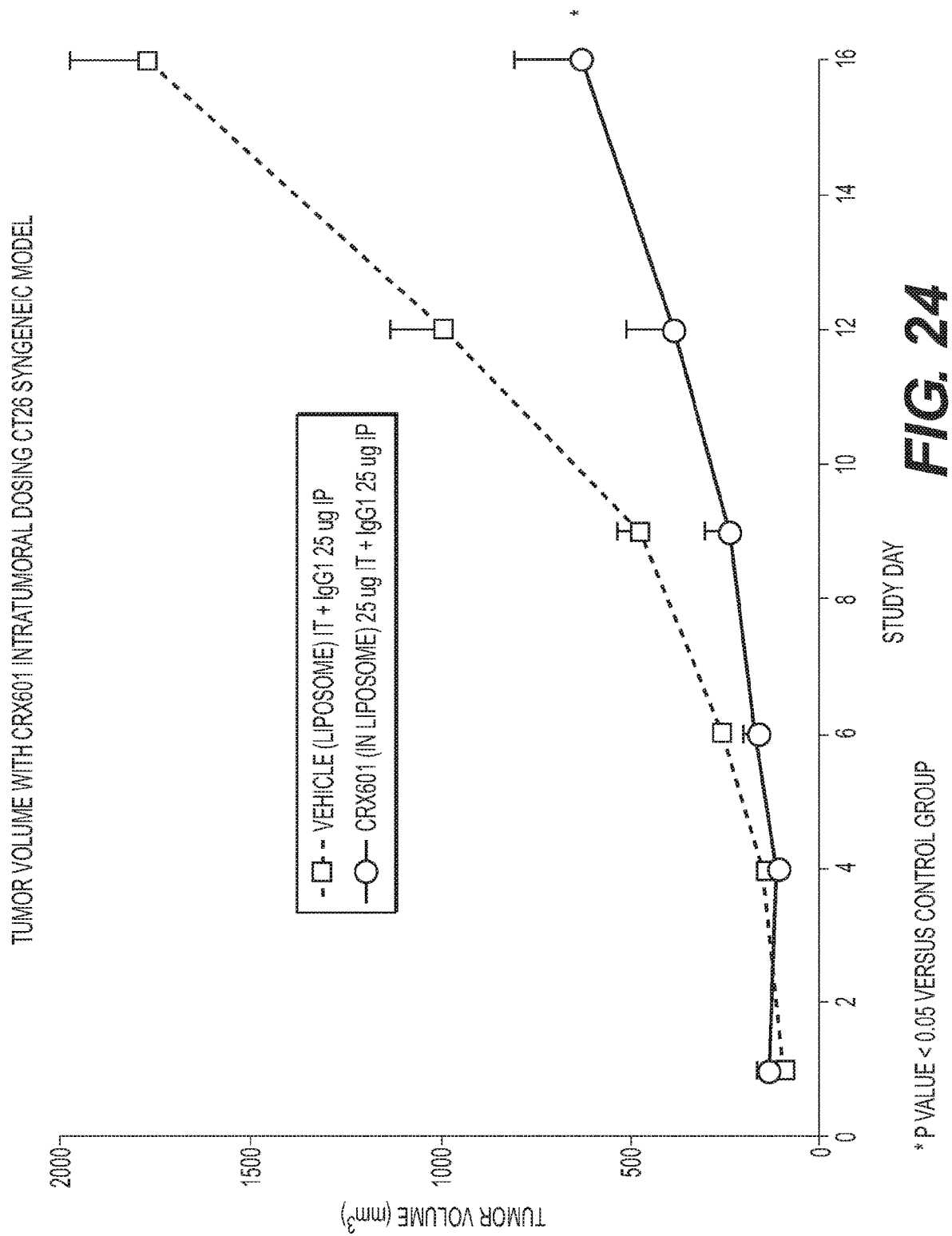
FIG. 24 is a graph showing anti-tumor activity of CRX-601 administered intratumorally in a CT26 Syngeneic mouse model.

Group 1: Vehicle (0.5% Glycerol/4% dextrose) dosed intravenous once per week for 3 doses total+Rat IgG1 25 ug/mouse dosed intraperontoneal twice per week for 6 doses total Group 2: CRX-601 25 ug/mouse (in 0.5% Glycerol/4% dextrose) dosed intravenous once per week for 3 doses total+Rat IgG1 25 ug/mouse dosed intraperontoneal twice per week for 6 doses total Group 5: Vehicle (DOPC/CHOL Liposome) dosed intratumoral once per week for 3 doses total+Rat IgG1 25 ug/mouse dosed intraperontoneal twice per week for 6 doses total Group 7: CRX-601 25 ug/mouse (in DOPC/CHOL Liposome) dosed intratumoral once per week for 3 doses total+ Rat IgG1 25 ug/mouse dosed intraperontoneal twice per week for 6 doses total Anti-tumor activity was assessed (as measured by tumor growth inhibition over time) for treatment groups 12 days after the initial dose. The sub-optimal monotherapy CRX-601 dose of 25 ug/mouse showed statistically significant (*p-values≤0.05) tumor growth inhibition when dosed intravenous (Group 2 FIG. 23) or intratumoral (Group 7, liposomal formulation FIG. 24) compared to corresponding control groups (Group 1 and Group 5 respectively).

Figure 25:
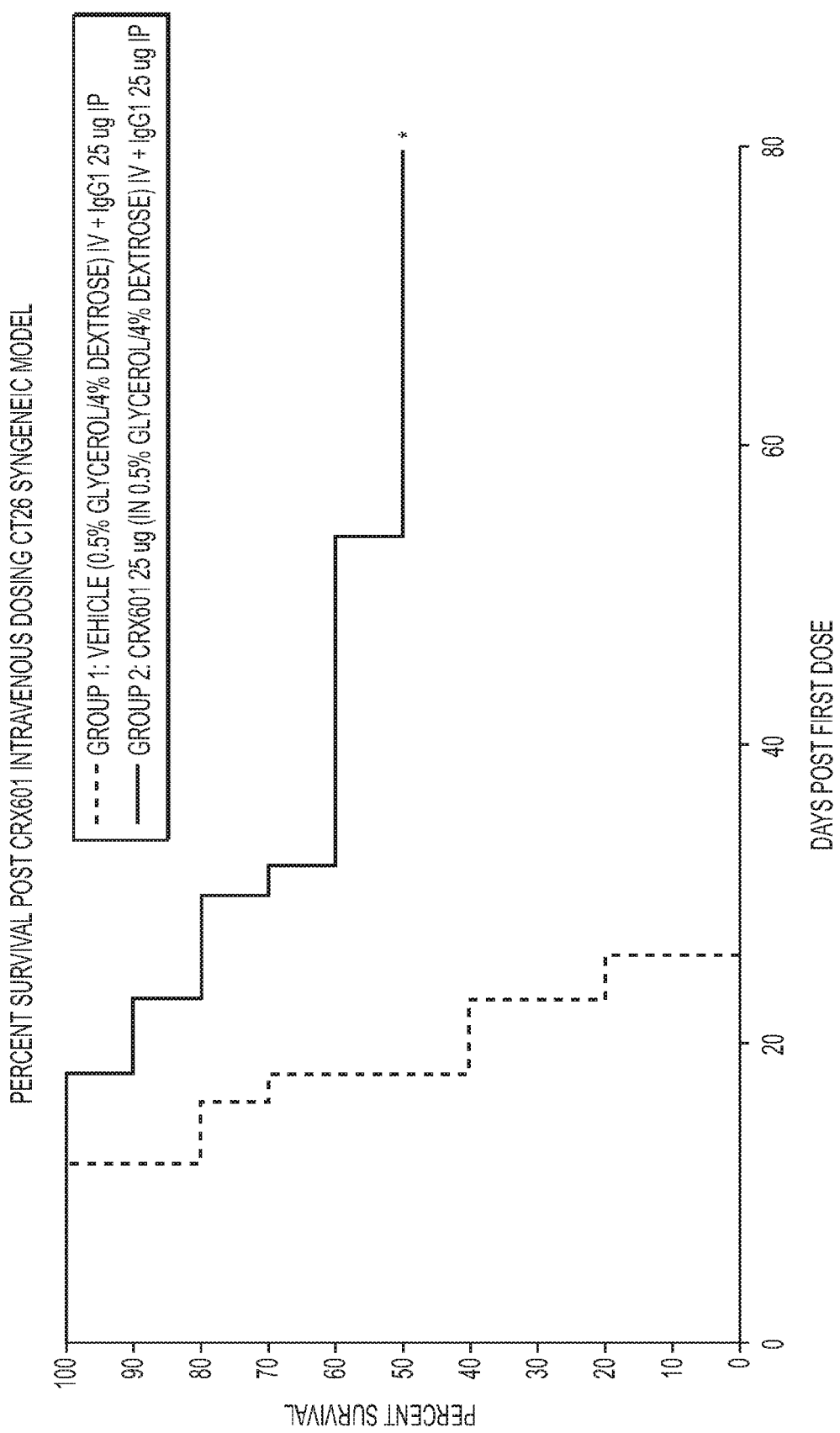
FIG. 25 is a graph showing survival benefits of CRX-601 administered intravenously in a CT26 Syngeneic mouse model
Figure 26:
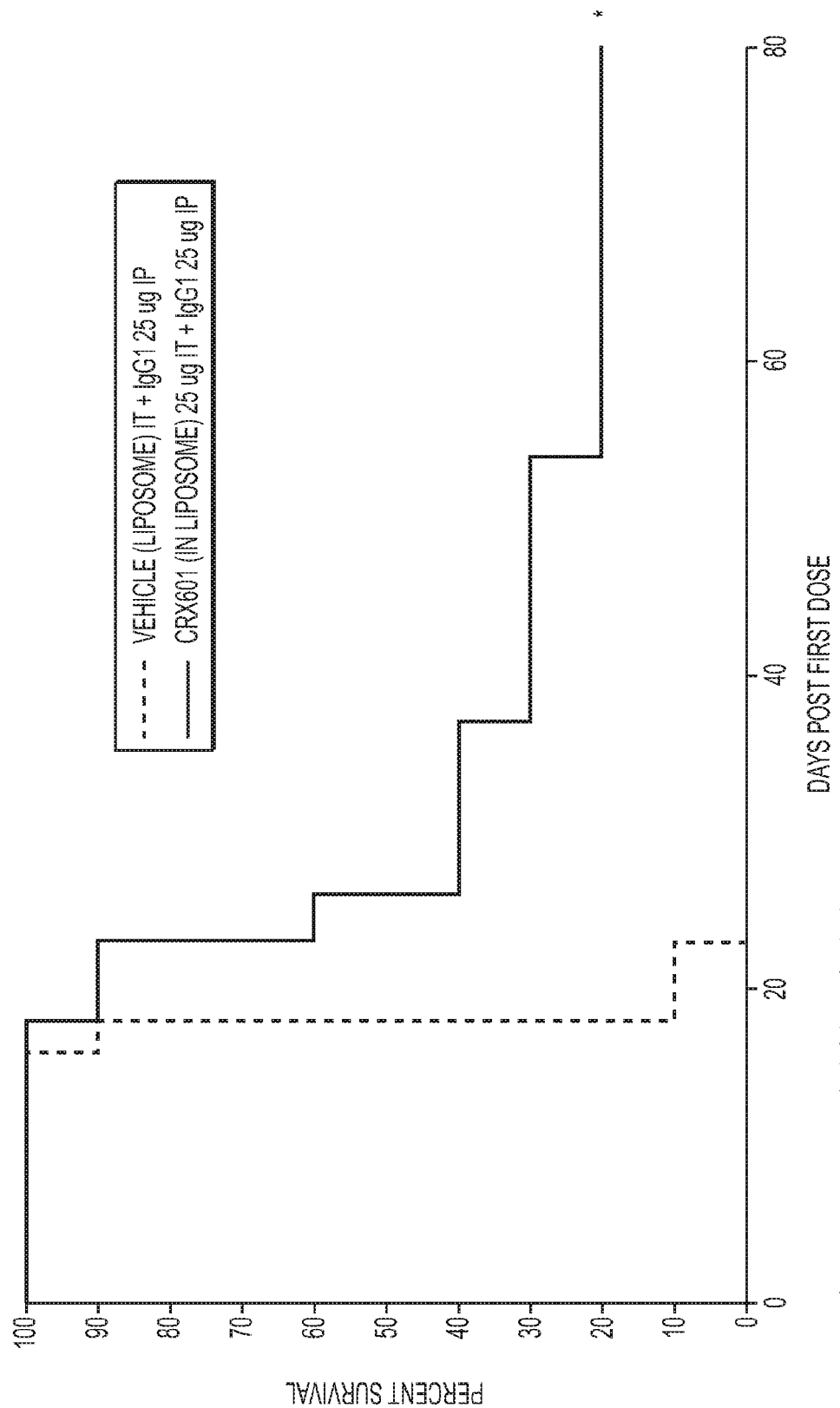
FIG. 26 is a graph showing survival benefits of CRX-601 administered intratumorally in a CT26 Syngeneic mouse model.
Figure 27:
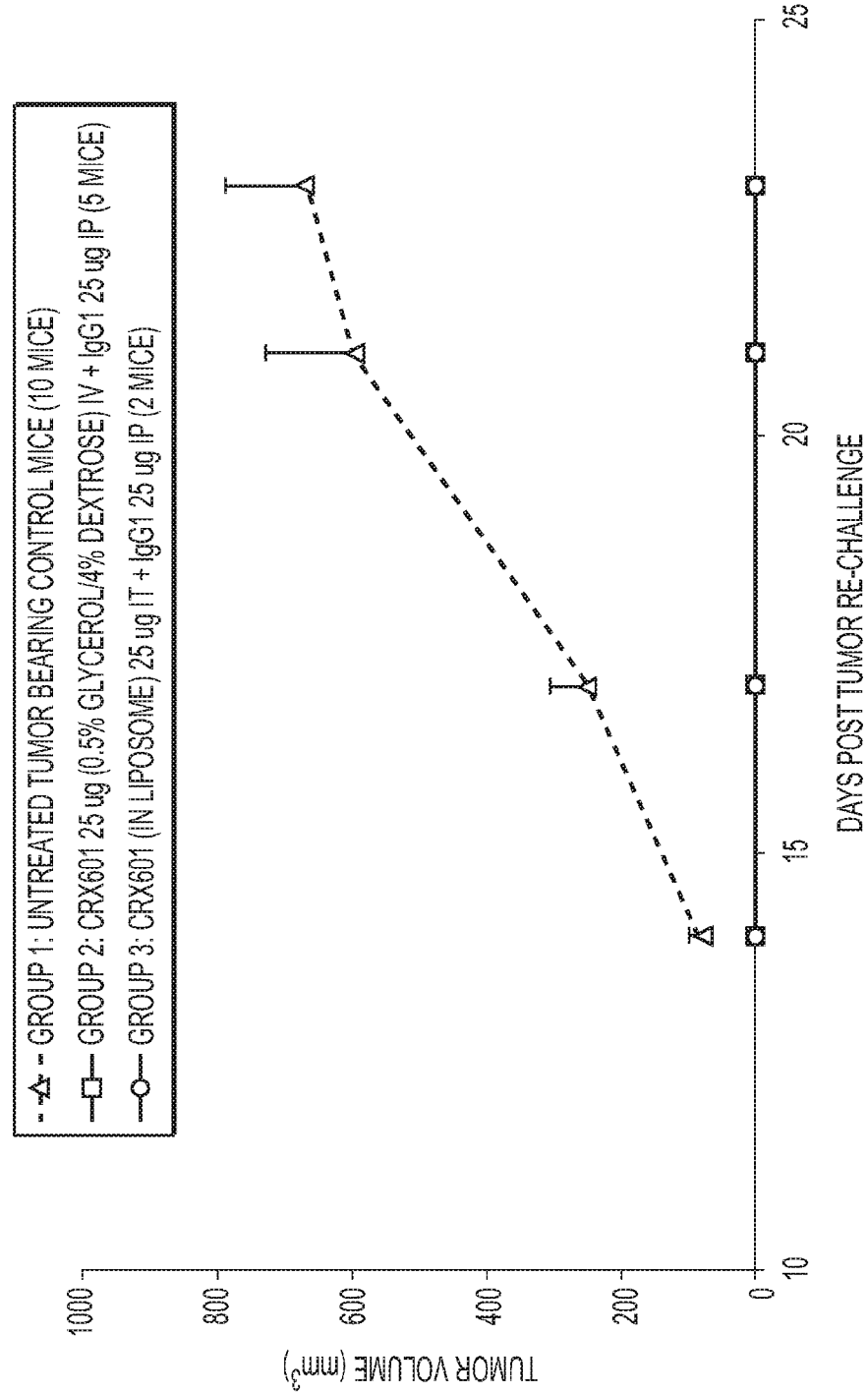
FIG. 27 is graph showing anti-tumor activity of CRX-601 administered intravenously or intratumorally in a CT26 Syngeneic mouse model.

In this CT-26 syngeneic mouse model study, survival advantage was also determined 80 days after the first dose. CRX-601 dosed as a monotherapy IV (Group 2), showed a statistically significant (*p-values≤0.05) increase in survival compared to control Group 1. (FIG. 25) Group 2 had 5 out of 10 mice showing full tumor regressions. CRX-601 dosed as a monotherapy intratumoral with the DOPC/CHOL liposome formulation (Group 7), showed a statistically significant (*p-values≤0.05) increase in survival compared to control Group 5. (FIG. 26). Naïve control mice and fully regressed tumor-free mice on day 80 were re-challenged with CT26 tumor cells. CT26 tumors grew as expected in naïve control mice, but were rejected with no tumor growth in the treatment group mice. This result indicates a persistent anti-tumor memory due to CRX-601. (FIG. 27) This lack of tumor growth indicates a persistent anti-tumor memory due to CRX-601.

Example 11 Abscopal Effects of CRX-601

Study 4

An abscopal effect is described as distant tumor regression after a local tumor treatment. In order to asses abscopal effects, mice were inoculated with 5×10$^4$ CT-26 cells on the left flank, and 5×10$^4$ CT-26 cells on the right flank as described in Materials and Methods for single tumor inoculation. Thus, in this study, each mouse possessed two tumors, one on the right flank, and one on the left flank. Mice were randomized into groups of 10 as shown below when tumor size reached approximately 100 mm$^3$ for the right flank, and left flank tumor size was similar. In a study designed to determine abscopal effect of CRX-601 activity alone and in combination with a therapeutic antibody, (combination data not shown) CRX-601 was dosed intratumoral (IT) in the left flank tumor only using a DOPC/CHOL liposomal formulation. Tumor size was monitored for both the right and left flank tumors. Results of the study provide evidence supporting the efficacy of administering CRX-601 alone for the treatment of cancer.

Figure 28:
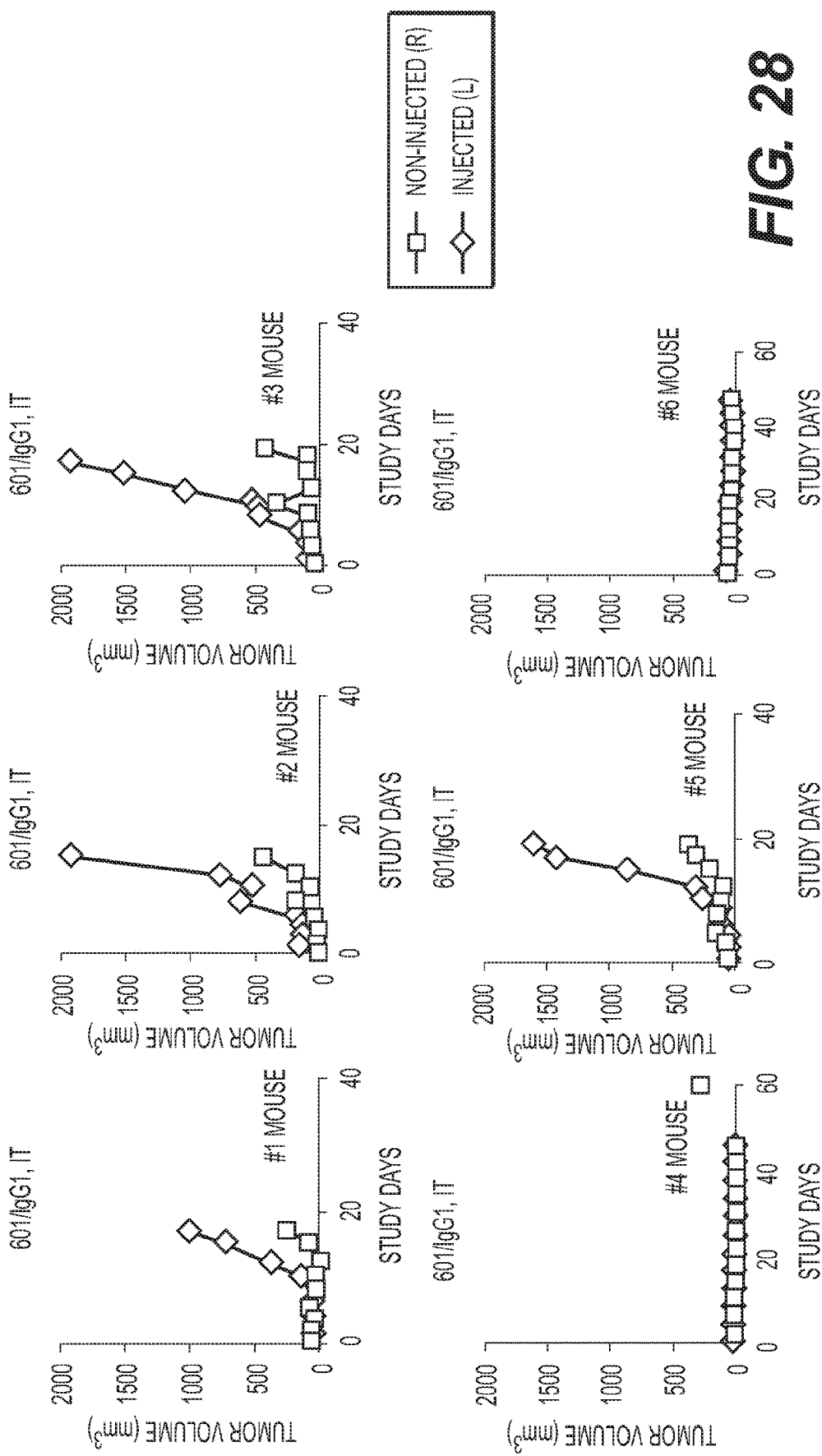
FIG. 28 shows graphs of anti-tumor activity in mice treated with a liposome formulation of CRX-601 administered intratumorally.
Figure 28:
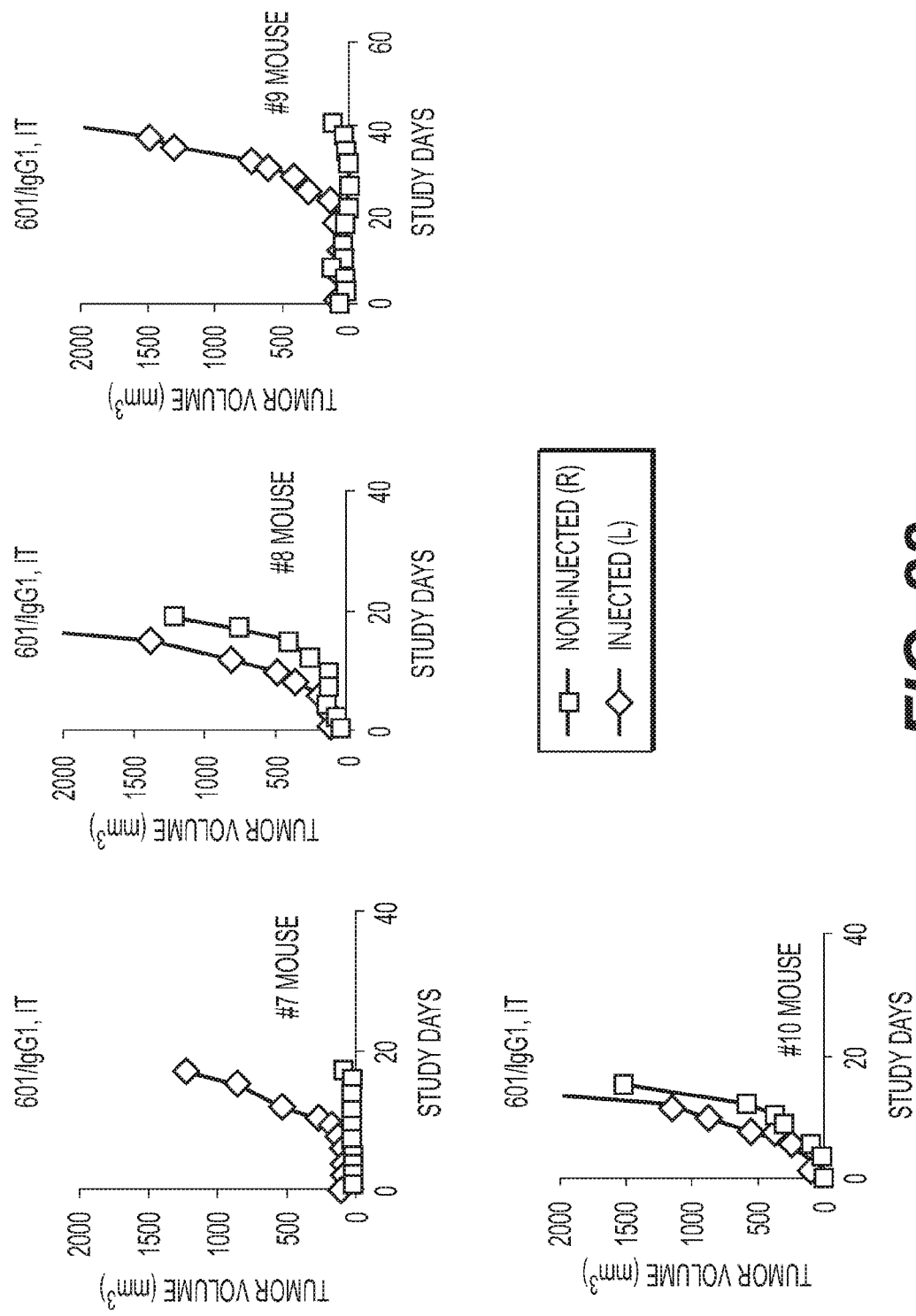

Group 1: Vehicle (DOPC/CHOL Liposome) dosed intratumoral once per week for 3 doses total+Rat IgG1 25 ug/mouse dosed intraperontoneal twice per week for 6 doses total Group 2 CRX-601 25 ug/mouse (in DOPC/CHOL Liposome) dosed intratumoral once per week for 3 doses total+ Rat IgG1 25 ug/mouse dosed intraperontoneal twice per week for 6 doses total Anti-tumor activity was assessed (as measured by tumor growth inhibition over time) for treatment groups. Mice were removed from study if either or both tumors reached 2,000 mm$^3$. By study day 60 post first dose, all mice remaining on study were completely tumor free, and abscopal effect and survival advantage was determined. Abscopal effect of CRX-601 was observed where the local left flank tumor IT injection resulted in distant right flank tumor regression. FIG. 28 showed that in group 2, 10 mice received liposomal CRX-601 intratumoral injections, 2 out 10 mice (mouse #4 and mouse #6) showed complete tumor regression on the treated tumor sites (dark grey line). both mouse #4 and mouse #6 also had complete tumor regression on the untreated distant tumor on the other flank (light grey line), which indicated that IT injection of CRX-601 resulted in abscopal effect (FIG. 28). CRX-601 (liposomal) IT injection resulted in a significant survival benefit compared to the control group (blank liposome+rat IgG1 IT, group 2, p=0.011, graph not shown)

Example 12 EMT6 Syngeneic Tumor Model

The in vivo anti-tumor efficacy of the TLR4 agonist (CRX-601) was assessed in the murine EMT6 breast epithelial syngeneic solid tumor model as a monotherapy versus control and anti-PD-1 treatment. Seven to eight week old female Balb/c mice (BALB/cAnNHsd, Envigo) were used in these studies. Murine EMT6 breast epithelial cells (ATCC catalog number lot # CRL-2755) were cultured in RPMI growth medium supplemented with 10% fetal bovine serum (FBS) in a humidified 37° C. incubator with 5% CO2. EMT6 cells cultured in logarithmic growth were harvested from tissue culture flasks and centrifuged for 5 minutes at 450×g at 4° C. for ten minutes to pellet cells. The supernatant was discarded, and cells were washed in ice cold phosphate buffered saline (PBS) without calcium and magnesium and centrifuged again for 5 minutes at 450×g at 4'C for ten minutes to pellet cells. The cells were resuspended in sterile RPMI media without FBS and adjusted to a cell concentration of 1×10$^6$ cells/ml. 100 µl of the cell stock was implanted via subcutaneous injection into the right flank of each Balb/c mouse. After seven or nine days when the average tumor size reached approximately 100 mm$^3$, mice were randomized into study cohorts according to tumor size and the first treatment dose was given. The TLR4 agonist (CRX-601) or vehicle was dosed via a systemic intravenous dose once per week for three total doses. The CRX-601 vehicle was 0.5% Glycerol/4% Dextrose, eE 810115-V. The rat anti-mouse PD-1 receptor antibody (clone RMP1-14, BioXCell catalog # BE0146, lot #5792-599016J1) or Rat IgG2a isotype control antibody (BioXCell catalog # BE0089,lot #601416M1B) was dosed via an intraperitoneal injection given every other day for a total of three doses, with the first dose given concurrently with the first CRX-601 dose. Caliper measurements were taken three times per week to assess tumor growth, and mice with tumors >2,000 mm$^3$ for 2 consecutive measurements or mice with tumors which formed open ulcers were removed from the study. Tumor volume was calculated using the formula (0.52)×(Length)×(Width2). All studies were conducted in accordance with the GSK Policy on the Care, Welfare and Treatment of Laboratory Animals and were reviewed by the Institutional Animal Care and Use Committee at GSK. To determine significance of tumor growth inhibition, tumor volumes 19 days post first dose were compared between the different treatment groups. Treatments were compared by standard ANOVA methods followed by FDR adjustment for multiplicity. Response is square root of volume, for homoscedasticity (equal variance) reasons. Kaplan-Meier (KM) method was carried out to estimate the survival probability of different treatment groups at a given time. For these survival analyses, "Death" means crossing the tumor volume cutoff (2000 mm3). "Survival" means proportion of mice not "Dead", and "Survival time" means days until "Death". If a mouse crossed the volume cutoff between two measurement days, then the day of "Death" was estimated by linear interpolation. If a mouse crossed the volume cutoff more than once, the first crossing was used. Treatments were compared by the standard log-rank test for two treatments. The log-rank p-values were adjusted for multiplicity using the FDR (false discovery rate) method. Significance was defined as FDR<=0.05. All calculations and graphs were done using R software, version 3.2.3.

The mouse cohorts were as follows:

Group 1: Vehicle+200 ug Rat IgG2a

Group 2: 25 ug CRX-601+200 ug Rat IgG2a

Group 3: Vehicle+200 ug anti-PD-1

With intravenous dosing, anti-tumor activity (as measured by tumor growth inhibition over time) was observed for the TLR4 agonist CRX-601 in the EMT6 syngeneic mouse tumor model. The 25 μg CRX-601 dosed mice showed statistically significant tumor growth inhibition 19 days after the initial dose compared to vehicle group 1 (**p-value<0.001), and compared to anti-PD-1 treatment group 3 (*p-value=0.041). Results are shown in FIG. 29. The anti-PD-1 treatment showed statistically significant tumor growth inhibition 19 days after the initial dose compared to vehicle group 1 (*p-value=0.03).

Mice treated with the TLR4 agonist CRX-601 in this study also showed a statistically significant increase in survival time. The 25 μg CRX-601 dosed mice showed a statistically significant (*p-value=0.03) increase in survival compared to vehicle group 1 by day 33 post EMT6 tumor cell inoculation. On this day, 6 mice from the 25 ug CRX-601 group remained on study. 4 mice were tumor free, while two mice possessed tumor volumes of 649 and 382 mm$^3$. The 200 ug anti-PD-1 dosed mice dosed mice did not show a statistically significant (p-value=0.199) increase in survival compared to vehicle group 1 by day 33 post EMT6 tumor cell inoculation. On this day, 5 mice from the anti-PD-1 group remained on study. 3 mice were tumor free, while two mice possessed tumor volumes of 1517 and 917 mm$^3$. Results are shown in FIG. 30.

We claim:

1. A method of treating cancer in a human in need thereof comprising administering a composition comprising a TLR4 agonist which is CRX-601, having the formula shown below:

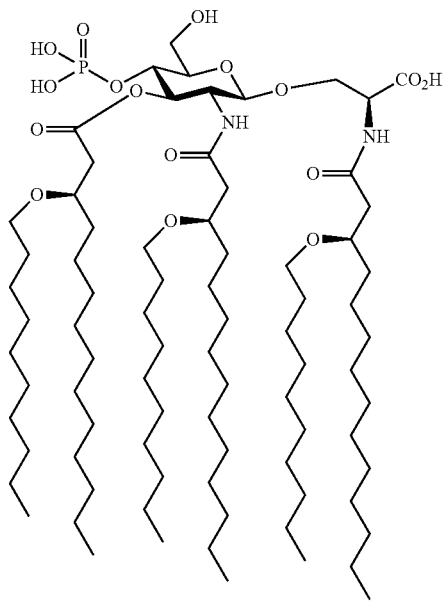

for treating cancer and combined with an anti-cancer agent, wherein the cancer is a solid tumor and selected from the group consisting of (1) primary and secondary metastatic forms of head and neck cancer and (2) carcinoma of the head and neck.

2. A method of treating cancer in a human in need thereof comprising administering a pharmaceutical composition comprising a therapeutically effective amount of an anti-cancer agent and a second pharmaceutical composition comprising a therapeutically effective amount of the TLR4 agonist, which CRX-601, having the formula shown below:

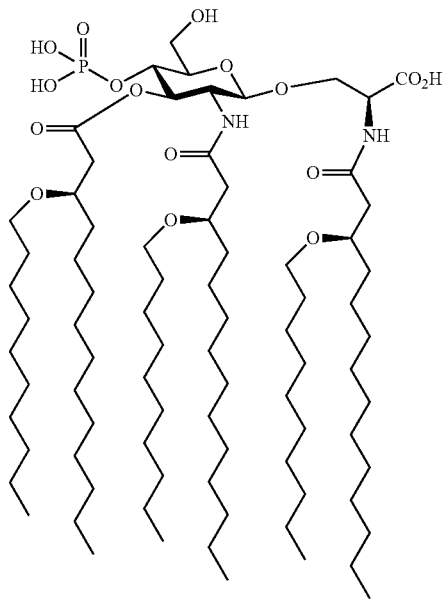

wherein the cancer is wherein the cancer is a solid tumor and selected from the group consisting of (1) primary and secondary metastatic forms of head and neck cancer and (2) carcinoma of the head and neck.

3. The method as claimed in claim 2, wherein the anti-cancer agent and the TLR4 agonist, CRX-601, are administered at the same time.

4. The method as claimed in claim 2, wherein the anti-cancer agent and the TLR4 agonist, CRX-601, are administered sequentially, in any order.

5. The method as claimed in claim 2, wherein the anti-cancer agent and the TLR4 agonist, CRX-601, are administered via a systemic intravenous dose.

6. The method as claimed in claim 2, wherein the anti-cancer agent, and the TLR4 agonist, CRX-601, is administered intratumorally.

7. The method as claimed in claim 2, wherein the anti-cancer agent is administered intratumorally, and the TLR4 agonist, CRX-601, is administered intravenously.

8. The method as claimed in claim 2, wherein the anti-cancer agent and the TLR4 agonist, CRX-601, are both administered intratumorally.

9. The method of claim 2, wherein anti-cancer agent is an anti PD-1 antibody.

* * * * *